US011213436B2

(12) United States Patent
Smith et al.

(10) Patent No.: US 11,213,436 B2
(45) Date of Patent: Jan. 4, 2022

(54) SUBSTRATES HAVING REPEATING PATTERNS OF APERTURES FOR ABSORBENT ARTICLES

(71) Applicant: The Procter & Gamble Company, Cincinnati, OH (US)

(72) Inventors: Alizha Victoria Smith, Wyoming, OH (US); Kelyn Anne Arora, Cincinnati, OH (US); Matthew Steven Ritter, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/733,554

(22) Filed: Jan. 3, 2020

(65) Prior Publication Data

US 2020/0139346 A1 May 7, 2020

Related U.S. Application Data

(63) Continuation of application No. 15/897,184, filed on Feb. 15, 2018, now abandoned.
(Continued)

(51) Int. Cl.
*B32B 3/24* (2006.01)
*B32B 5/26* (2006.01)
(Continued)

(52) U.S. Cl.
CPC ........ *A61F 13/5126* (2013.01); *A61F 13/512* (2013.01); *A61F 13/5116* (2013.01); *A61F 13/5122* (2013.01); *A61F 13/5123* (2013.01); *A61F 13/51121* (2013.01); *A61F 13/51394* (2013.01); *A61F 13/51456* (2013.01); *B32B 3/266* (2013.01); *B32B 5/02* (2013.01); *B32B 5/26* (2013.01); *B32B 5/266* (2021.05); *B32B 5/267* (2021.05); *A61F 13/15617* (2013.01); *A61F 13/515* (2013.01); *A61F 13/51113* (2013.01); *A61F 2013/15959* (2013.01); *A61F 2013/5127* (2013.01); *A61F 2013/51042* (2013.01); *A61F 2013/51178* (2013.01);
(Continued)

(58) Field of Classification Search
None
See application file for complete search history.

(56) References Cited

U.S. PATENT DOCUMENTS

D116,633 S * 9/1939 Rubner ................. A61F 13/511
D5/37
3,137,893 A 6/1964 Gelpke
(Continued)

FOREIGN PATENT DOCUMENTS

CA 2182304 A1 1/1997
CA 2183776 A1 3/1997
(Continued)

OTHER PUBLICATIONS

Machine Translation of JP-2010051697-A, Mar. 2010 (Year: 2010).*
(Continued)

*Primary Examiner* — Jeffrey A Vonch
(74) *Attorney, Agent, or Firm* — Christian M. Best

(57) ABSTRACT

The present disclosure is directed to substrates or topsheets having repeating patterns of apertures for absorbent articles. Each of the repeat units comprises at least three apertures.

20 Claims, 25 Drawing Sheets

Related U.S. Application Data

(60) Provisional application No. 62/459,765, filed on Feb. 16, 2017.

(51) Int. Cl.
| | |
|---|---|
| *A61F 13/511* | (2006.01) |
| *A61F 13/512* | (2006.01) |
| *A61F 13/513* | (2006.01) |
| *A61F 13/514* | (2006.01) |
| *B32B 3/26* | (2006.01) |
| *B32B 5/02* | (2006.01) |
| *B01J 20/28* | (2006.01) |
| *B01J 20/32* | (2006.01) |
| *A61F 13/15* | (2006.01) |
| *A61F 13/51* | (2006.01) |
| *A61F 13/515* | (2006.01) |

(52) U.S. Cl.
CPC .......... *A61F 2013/51377* (2013.01); *B01J 20/28038* (2013.01); *B01J 20/28095* (2013.01); *B01J 20/3297* (2013.01); *B32B 2307/41* (2013.01); *B32B 2307/726* (2013.01); *B32B 2307/728* (2013.01); *B32B 2307/73* (2013.01); *B32B 2555/02* (2013.01); *Y10T 428/24298* (2015.01); *Y10T 428/24331* (2015.01); *Y10T 442/659* (2015.04); *Y10T 442/66* (2015.04); *Y10T 442/681* (2015.04); *Y10T 442/699* (2015.04)

(56) References Cited

U.S. PATENT DOCUMENTS

| | | |
|---|---|---|
| 3,559,648 A | 2/1971 | Mason, Jr. |
| 3,655,501 A | 4/1972 | Tesch |
| 3,673,026 A | 6/1972 | Brown |
| 3,814,101 A | 6/1974 | Kozak |
| 3,849,845 A | 11/1974 | Obenaus |
| 3,860,003 A | 1/1975 | Buell |
| 3,886,941 A | 6/1975 | Duane et al. |
| 3,890,974 A | 6/1975 | Kozak |
| D237,114 S * | 10/1975 | Fröidh et al. ............... D24/126 |
| 3,911,173 A | 10/1975 | Sprague, Jr. |
| 3,929,135 A | 12/1975 | Thompson |
| D238,449 S * | 1/1976 | Matsumoto .................. D5/57 |
| D239,137 S * | 3/1976 | Appleman .................. D5/57 |
| D240,563 S * | 7/1976 | Whitehead et al. .......... D24/125 |
| D240,564 S * | 7/1976 | Whitehead et al. .......... D24/125 |
| D247,368 S * | 2/1978 | Whitehead .................. 604/358 |
| D247,371 S * | 2/1978 | Whitehead .................. 604/358 |
| 4,137,180 A | 1/1979 | Naik et al. |
| 4,199,464 A | 4/1980 | Cambre |
| D259,219 S * | 5/1981 | Bates ........................... D5/57 |
| 4,306,559 A | 12/1981 | Nishizawa et al. |
| 4,323,069 A | 4/1982 | Ahr et al. |
| 4,324,246 A | 4/1982 | Mullane et al. |
| 4,327,730 A | 5/1982 | Sorensen |
| D276,184 S * | 10/1984 | Whitehead .................. D24/125 |
| D276,368 S * | 11/1984 | Whitehead .................. D24/125 |
| 4,573,986 A | 3/1986 | Minetola et al. |
| 4,588,630 A | 5/1986 | Shimalla |
| 4,609,518 A | 9/1986 | Curro et al. |
| 4,610,678 A | 9/1986 | Goldman et al. |
| 4,623,340 A | 11/1986 | Luceri |
| 4,629,643 A | 12/1986 | Curro et al. |
| D287,637 S * | 1/1987 | Grasso ........................ D24/125 |
| 4,637,819 A | 1/1987 | Ouellette et al. |
| 4,673,402 A | 6/1987 | Weisman et al. |
| 4,676,784 A | 6/1987 | Erdman et al. |
| 4,704,112 A | 11/1987 | Suzuki et al. |
| 4,741,941 A | 5/1988 | Englebert et al. |
| 4,780,352 A | 10/1988 | Palumbo et al. |
| 4,781,710 A | 11/1988 | Megison et al. |
| 4,785,996 A | 11/1988 | Ziecker et al. |
| 4,798,604 A | 1/1989 | Carter |
| 4,818,587 A | 4/1989 | Ejima et al. |
| 4,834,735 A | 5/1989 | Alemany et al. |
| 4,840,829 A | 6/1989 | Suzuki et al. |
| 4,842,666 A | 6/1989 | Werenicz |
| 4,844,965 A * | 7/1989 | Foxman .................. A61F 5/485 428/91 |
| 4,888,231 A | 12/1989 | Angstadt |
| 4,908,026 A * | 3/1990 | Sukiennik .......... A61F 13/15203 604/378 |
| 4,950,264 A | 8/1990 | Osborn, III |
| 5,108,820 A | 4/1992 | Kaneko et al. |
| 5,122,407 A | 6/1992 | Yeo et al. |
| 5,147,345 A | 9/1992 | Young et al. |
| 5,151,092 A | 9/1992 | Buell et al. |
| 5,226,992 A | 7/1993 | Morman |
| 5,234,423 A | 8/1993 | Alemany et al. |
| 5,296,622 A | 3/1994 | Uphues et al. |
| D349,159 S | 7/1994 | Huffman |
| D350,196 S * | 8/1994 | Huffman ..................... D24/124 |
| D350,197 S * | 8/1994 | Huffman ..................... D24/124 |
| H1377 H | 11/1994 | Perry |
| 5,369,858 A | 12/1994 | Gilmore et al. |
| 5,370,764 A | 12/1994 | Alikhan |
| D354,856 S * | 1/1995 | Schulz ........................... D5/53 |
| 5,382,773 A | 1/1995 | Kurihara et al. |
| 5,415,640 A | 5/1995 | Kirby et al. |
| 5,418,045 A | 5/1995 | Pike et al. |
| 5,433,715 A | 7/1995 | Tanzer et al. |
| 5,437,653 A | 8/1995 | Gilman et al. |
| D362,120 S | 9/1995 | Suskind et al. |
| D363,610 S * | 10/1995 | Saffran ......................... D5/53 |
| 5,456,982 A | 10/1995 | Hansen et al. |
| 5,485,662 A | 1/1996 | Hodges, Jr. et al. |
| D367,764 S * | 3/1996 | Makoui ......................... D5/53 |
| D368,587 S * | 4/1996 | Schulz ........................... D5/53 |
| 5,503,076 A | 4/1996 | Yeo |
| 5,518,801 A | 5/1996 | Chappell et al. |
| 5,520,673 A | 5/1996 | Yarbrough et al. |
| 5,536,555 A | 7/1996 | Zelazoski et al. |
| 5,571,096 A | 11/1996 | Dobrin et al. |
| 5,573,830 A * | 11/1996 | Schulz .................... B31F 1/07 162/109 |
| D377,419 S * | 1/1997 | Schulz ........................... D5/27 |
| 5,597,645 A | 1/1997 | Pike et al. |
| 5,599,335 A | 2/1997 | Goldman et al. |
| 5,605,749 A | 2/1997 | Pike et al. |
| 5,607,760 A | 3/1997 | Roe |
| 5,609,587 A | 3/1997 | Roe |
| 5,628,097 A | 5/1997 | Benson et al. |
| 5,628,737 A | 5/1997 | Dobrin et al. |
| 5,635,191 A | 6/1997 | Roe et al. |
| 5,643,588 A | 7/1997 | Roe et al. |
| D382,162 S * | 8/1997 | Ertolacci ........................ D5/53 |
| D382,713 S * | 8/1997 | Giesler, Sr. .................... D5/53 |
| 5,660,788 A | 8/1997 | Gray et al. |
| D384,210 S * | 9/1997 | du Grosriez .................... D5/53 |
| 5,665,083 A | 9/1997 | Igaue et al. |
| 5,667,562 A | 9/1997 | Midkiff |
| 5,667,619 A | 9/1997 | Alikhan |
| 5,704,101 A | 1/1998 | Majors et al. |
| 5,709,735 A | 1/1998 | Midkiff et al. |
| 5,714,107 A | 2/1998 | Levy et al. |
| 5,718,698 A | 2/1998 | Dobrin et al. |
| 5,731,061 A | 3/1998 | Bezier |
| 5,735,984 A | 4/1998 | Hoff et al. |
| H1732 H | 6/1998 | Johnson |
| 5,759,990 A | 6/1998 | Wahl et al. |
| 5,770,144 A | 6/1998 | James et al. |
| D395,955 S * | 7/1998 | du Grosriez .................... D5/53 |
| 5,780,155 A | 7/1998 | Ishizawa et al. |
| 5,797,894 A | 8/1998 | Cadieux et al. |
| 5,804,021 A | 9/1998 | Abuto et al. |
| 5,824,352 A | 10/1998 | Yang et al. |
| D402,475 S * | 12/1998 | Mattheeussen ................ D5/53 |
| 5,846,230 A | 12/1998 | Osborn, III et al. |
| 5,873,968 A | 2/1999 | Pike et al. |
| 5,874,160 A | 2/1999 | Keck |

(56) References Cited

U.S. PATENT DOCUMENTS

| | | | |
|---|---|---|---|
| D406,791 S * | 3/1999 | Schulz | D5/53 |
| 5,885,267 A | 3/1999 | Mishima et al. | |
| D407,902 S * | 4/1999 | Schulz | D5/53 |
| D408,152 S * | 4/1999 | Wilhelm | D5/53 |
| 5,895,380 A | 4/1999 | Turi et al. | |
| 5,897,541 A | 4/1999 | Uitenbroek et al. | |
| 5,897,543 A | 4/1999 | Francis | |
| 5,914,084 A | 6/1999 | Benson et al. | |
| 5,916,661 A | 6/1999 | Benson et al. | |
| 5,919,177 A | 7/1999 | Georger et al. | |
| D412,574 S * | 8/1999 | Trombetta | D24/125 |
| D412,575 S * | 8/1999 | Trombetta | D24/125 |
| D412,980 S * | 8/1999 | Trombetta | D24/125 |
| D412,981 S * | 8/1999 | Trombetta | D24/125 |
| 5,941,864 A | 8/1999 | Roe | |
| 5,965,468 A | 10/1999 | Marmon et al. | |
| 5,968,025 A | 10/1999 | Roe et al. | |
| 5,990,376 A | 11/1999 | Inoue et al. | |
| 5,998,696 A | 12/1999 | Schone | |
| 6,015,936 A | 1/2000 | Takai et al. | |
| 6,025,535 A | 2/2000 | Octavio | |
| 6,030,372 A | 2/2000 | Buell et al. | |
| D421,341 S * | 3/2000 | Bak | D5/32 |
| D426,303 S * | 6/2000 | Weyenberg | D24/124 |
| D426,709 S * | 6/2000 | Latchoo | D5/25 |
| D426,887 S * | 6/2000 | Rubio | D24/125 |
| D426,889 S * | 6/2000 | Bissah | D24/125 |
| 6,093,871 A | 7/2000 | Takai et al. | |
| D429,893 S * | 8/2000 | Jahner | D5/53 |
| D430,406 S * | 9/2000 | Ingalls | D5/53 |
| D430,407 S * | 9/2000 | Ingalls | D5/53 |
| D430,665 S * | 9/2000 | Kirkbride | D24/125 |
| 6,114,595 A | 9/2000 | Moore et al. | |
| 6,117,523 A | 9/2000 | Sugahara | |
| 6,117,524 A | 9/2000 | Hisanaka et al. | |
| 6,120,488 A * | 9/2000 | VanRijswijck | A61F 13/494 604/364 |
| 6,129,972 A * | 10/2000 | McNeil | D21H 27/40 428/154 |
| D433,572 S * | 11/2000 | Bissah | D5/37 |
| D434,568 S * | 12/2000 | Bissah | D5/39 |
| D434,849 S * | 12/2000 | Kirkbride | D24/125 |
| 6,159,881 A | 12/2000 | Datta et al. | |
| 6,168,849 B1 | 1/2001 | Braverman et al. | |
| D439,057 S | 3/2001 | Bissah et al. | |
| D439,660 S * | 3/2001 | Velazquez | D24/124 |
| D439,661 S * | 3/2001 | Velazquez | D24/125 |
| 6,203,905 B1 | 3/2001 | Pike | |
| 6,206,865 B1 | 3/2001 | Chen et al. | |
| 6,228,462 B1 | 5/2001 | Lee et al. | |
| 6,231,555 B1 * | 5/2001 | Lynard | A61F 13/5126 604/364 |
| 6,261,666 B1 * | 7/2001 | Enderby | B31F 1/07 156/209 |
| 6,262,331 B1 | 7/2001 | Nakahata et al. | |
| 6,270,623 B1 | 8/2001 | Goda et al. | |
| 6,271,192 B1 | 8/2001 | Verstrat et al. | |
| 6,274,218 B1 | 8/2001 | Shimizu | |
| 6,274,237 B1 | 8/2001 | Nakajima et al. | |
| D448,078 S * | 9/2001 | Deoliveira | D24/124 |
| D448,478 S * | 9/2001 | Deoliveira | D24/124 |
| 6,303,208 B1 | 10/2001 | Pelkie | |
| D451,682 S * | 12/2001 | Jahner | D5/25 |
| 6,326,430 B1 | 12/2001 | Berte | |
| 6,344,111 B1 * | 2/2002 | Wilhelm | B31F 1/07 162/101 |
| 6,348,541 B1 | 2/2002 | Kanda et al. | |
| 6,361,781 B2 | 3/2002 | Lorant | |
| 6,376,456 B1 | 4/2002 | Murphy et al. | |
| 6,410,823 B1 | 6/2002 | Daley et al. | |
| 6,413,920 B1 | 7/2002 | Bettiol et al. | |
| 6,452,064 B1 | 9/2002 | Thoren et al. | |
| 6,454,747 B1 | 9/2002 | Shimada et al. | |
| 6,454,989 B1 | 9/2002 | Neely et al. | |
| 6,464,831 B1 * | 10/2002 | Trokhan | D21F 11/006 162/109 |
| 6,468,626 B1 | 10/2002 | Takai et al. | |
| 6,475,600 B1 | 11/2002 | Morman et al. | |
| 6,479,130 B1 | 11/2002 | Takai et al. | |
| 6,494,920 B1 | 12/2002 | Weuthen et al. | |
| 6,498,284 B1 | 12/2002 | Roe | |
| 6,506,473 B1 | 1/2003 | Hisanaka et al. | |
| 6,528,439 B1 | 3/2003 | Stokes et al. | |
| 6,534,149 B1 | 3/2003 | Daley et al. | |
| 6,610,391 B2 | 8/2003 | Molee | |
| 6,620,777 B2 | 9/2003 | Heibel et al. | |
| 6,632,504 B1 | 10/2003 | Gillespie et al. | |
| 6,649,547 B1 | 11/2003 | Arnold et al. | |
| 6,676,646 B2 | 1/2004 | Bast et al. | |
| 6,713,159 B1 | 3/2004 | Blenke et al. | |
| 6,716,441 B1 | 4/2004 | Osborne et al. | |
| 6,846,561 B1 | 1/2005 | Gownder et al. | |
| 6,849,065 B2 | 2/2005 | Schmidt et al. | |
| 6,849,319 B2 | 2/2005 | Cree et al. | |
| D506,317 S * | 6/2005 | Hallberg | D5/57 |
| D506,618 S * | 6/2005 | Seguinot | D5/27 |
| D507,413 S * | 7/2005 | Farahat | D5/20 |
| 6,916,969 B1 | 7/2005 | Helmfridsson et al. | |
| 6,924,261 B2 | 8/2005 | Grandmaire et al. | |
| D512,505 S * | 12/2005 | Vinson | D24/124 |
| 6,992,058 B2 | 1/2006 | Grandmaire et al. | |
| 6,996,851 B2 | 2/2006 | Nordness et al. | |
| 7,005,558 B1 | 2/2006 | Johansson et al. | |
| D517,816 S * | 3/2006 | Dwiggins | D5/25 |
| 7,033,340 B1 | 4/2006 | Muscat et al. | |
| 7,056,404 B2 | 6/2006 | McFall | |
| 7,063,895 B2 | 6/2006 | Rodrigues et al. | |
| 7,067,711 B2 | 6/2006 | Kuroda et al. | |
| D529,607 S * | 10/2006 | Lindner | D24/124 |
| 7,118,639 B2 | 10/2006 | Delucia et al. | |
| D545,572 S * | 7/2007 | Barkey | D5/37 |
| D546,068 S * | 7/2007 | Vidal | D5/37 |
| D551,343 S * | 9/2007 | Harsjo | D24/124 |
| D561,481 S * | 2/2008 | Mecchi | D5/57 |
| 7,371,919 B1 | 5/2008 | Busam et al. | |
| 7,378,033 B2 | 5/2008 | Harrison et al. | |
| 7,381,417 B2 | 6/2008 | Gamez-Garcia | |
| D581,170 S * | 11/2008 | Delaney | D5/53 |
| D581,524 S * | 11/2008 | Macaulay | D24/124 |
| D583,464 S * | 12/2008 | Francoeur | D24/124 |
| D584,401 S | 1/2009 | Francoeur | |
| D585,649 S * | 2/2009 | Bachmann | D5/39 |
| D586,564 S * | 2/2009 | Enderby | D5/39 |
| D612,491 S * | 3/2010 | Sullivan Conrad | D24/124 |
| 7,803,244 B2 | 9/2010 | Siqueira et al. | |
| 7,806,880 B2 | 10/2010 | Roe et al. | |
| D632,496 S * | 2/2011 | Nugent | D5/32 |
| D632,896 S * | 2/2011 | Sanders | D5/58 |
| 7,887,522 B2 | 2/2011 | Roe et al. | |
| 7,967,801 B2 | 6/2011 | Hammons et al. | |
| 7,981,850 B2 | 7/2011 | Doi et al. | |
| 8,022,267 B2 | 9/2011 | Hellstroem et al. | |
| D651,410 S * | 1/2012 | Nugent | D5/25 |
| D656,740 S * | 4/2012 | Nugent | D5/25 |
| 8,186,296 B2 | 5/2012 | Brown et al. | |
| 8,188,022 B2 | 5/2012 | Sengupta et al. | |
| 8,211,414 B2 | 7/2012 | Chen et al. | |
| 8,226,625 B2 | 7/2012 | Turner et al. | |
| 8,226,626 B2 | 7/2012 | Turner et al. | |
| 8,227,660 B2 | 7/2012 | Hara et al. | |
| 8,231,595 B2 | 7/2012 | Turner et al. | |
| 8,251,965 B2 | 8/2012 | Costea et al. | |
| D668,332 S * | 10/2012 | Hough | D24/124 |
| D673,780 S * | 1/2013 | Van Straten | D5/57 |
| 8,388,594 B2 | 3/2013 | Turner et al. | |
| D682,420 S * | 5/2013 | Abram | D24/124 |
| 8,454,571 B2 | 6/2013 | Rezai et al. | |
| 8,524,649 B2 | 9/2013 | Leyrer et al. | |
| D692,130 S * | 10/2013 | Biggs | D24/125 |
| D694,024 S * | 11/2013 | Dwiggins | D5/57 |
| D708,444 S * | 7/2014 | Love | D5/4 |
| 9,018,154 B2 | 4/2015 | Blondel | |
| 9,034,230 B2 | 5/2015 | Qureshi et al. | |

(56) References Cited

U.S. PATENT DOCUMENTS

| | | | |
|---|---|---|---|
| 9,044,353 B2 | 6/2015 | Stone et al. | |
| 9,149,968 B2 | 10/2015 | Wilhelm et al. | |
| 9,237,973 B2 | 1/2016 | Abuto et al. | |
| D750,385 S * | 3/2016 | Martin | D5/39 |
| D750,386 S * | 3/2016 | Martin | D5/39 |
| 9,441,188 B2 | 9/2016 | Schramm, Jr. et al. | |
| D768,393 S * | 10/2016 | Ellis | D5/53 |
| D777,451 S * | 1/2017 | Hunt | D5/2 |
| 9,550,309 B2 | 1/2017 | Gibson et al. | |
| D778,436 S | 2/2017 | Coslett et al. | |
| 2001/0005540 A1 | 6/2001 | Hisanaka et al. | |
| 2001/0008683 A1 * | 7/2001 | Takai | A61F 13/42 428/196 |
| 2001/0053901 A1 | 12/2001 | Mizutani et al. | |
| 2002/0013563 A1 | 1/2002 | Desai et al. | |
| 2002/0016122 A1 | 2/2002 | Curro et al. | |
| 2002/0022817 A1 | 2/2002 | Ishikawa | |
| 2002/0028624 A1 | 3/2002 | Mizutani et al. | |
| 2002/0034912 A1 | 3/2002 | Curro et al. | |
| 2002/0062113 A1 | 5/2002 | Thomas et al. | |
| 2002/0062115 A1 | 5/2002 | Wada et al. | |
| 2002/0081927 A1 | 6/2002 | Maldonado et al. | |
| 2002/0089079 A1 | 7/2002 | Shelley et al. | |
| 2002/0098762 A1 | 7/2002 | Shelley et al. | |
| 2002/0098764 A1 | 7/2002 | Mleziva et al. | |
| 2002/0147435 A1 | 10/2002 | Coles et al. | |
| 2002/0172371 A1 | 11/2002 | Baker et al. | |
| 2002/0182371 A1 | 12/2002 | Soon et al. | |
| 2002/0182396 A1 | 12/2002 | Delucia et al. | |
| 2002/0193032 A1 | 12/2002 | Newkirk et al. | |
| 2003/0003269 A1 | 1/2003 | Lee et al. | |
| 2003/0004481 A1 | 1/2003 | Matsuoka et al. | |
| 2003/0011099 A1 | 1/2003 | Maldonado et al. | |
| 2003/0021951 A1 | 1/2003 | Desai et al. | |
| 2003/0026945 A1 | 2/2003 | Lasko | |
| 2003/0028165 A1 | 2/2003 | Curro et al. | |
| 2003/0077430 A1 | 4/2003 | Grimm et al. | |
| 2003/0082377 A1 | 5/2003 | Hartzog et al. | |
| 2003/0082979 A1 | 5/2003 | Bean et al. | |
| 2003/0104748 A1 | 6/2003 | Brown et al. | |
| 2003/0109839 A1 | 6/2003 | Costea et al. | |
| 2003/0125687 A1 | 7/2003 | Gubernick et al. | |
| 2003/0145517 A1 | 8/2003 | Miller | |
| 2003/0149412 A1 | 8/2003 | Damaghi et al. | |
| 2003/0187415 A1 | 10/2003 | Kudo et al. | |
| 2003/0217945 A1 | 11/2003 | Kiene et al. | |
| 2003/0232558 A1 * | 12/2003 | Moody, III | D04H 1/49 442/327 |
| 2004/0029479 A1 * | 2/2004 | Snider | D04H 1/495 442/387 |
| 2004/0038851 A1 | 2/2004 | Aubay et al. | |
| 2004/0043189 A1 | 3/2004 | Huang | |
| 2004/0065208 A1 | 4/2004 | Hart et al. | |
| 2004/0067709 A1 | 4/2004 | Kishine et al. | |
| 2004/0071716 A1 | 4/2004 | Jansen et al. | |
| 2004/0081804 A1 * | 4/2004 | Basler | B31F 1/07 428/174 |
| 2004/0087924 A1 * | 5/2004 | Sroda | A61F 13/51121 604/367 |
| 2004/0092902 A1 | 5/2004 | Schuehle et al. | |
| 2004/0116027 A1 | 6/2004 | Termonia et al. | |
| 2004/0116322 A1 | 6/2004 | Manakopoulos et al. | |
| 2004/0118811 A1 | 6/2004 | Stone et al. | |
| 2004/0122396 A1 | 6/2004 | Maldonado et al. | |
| 2004/0122404 A1 | 6/2004 | Meyer et al. | |
| 2004/0127128 A1 | 7/2004 | Thomas | |
| 2004/0127875 A1 | 7/2004 | Hammons et al. | |
| 2004/0161586 A1 | 8/2004 | Cree et al. | |
| 2004/0162536 A1 | 8/2004 | Becker et al. | |
| 2004/0170813 A1 | 9/2004 | Digiacomantonio et al. | |
| 2004/0176734 A1 | 9/2004 | Rasmussen et al. | |
| 2004/0181199 A1 | 9/2004 | Moberg-Alehammar et al. | |
| 2004/0204337 A1 | 10/2004 | Corona, III et al. | |
| 2004/0209042 A1 | 10/2004 | Peacock et al. | |
| 2004/0241399 A1 * | 12/2004 | Marmon | D04H 1/559 428/196 |
| 2004/0265533 A1 * | 12/2004 | Hoying | A61F 13/51305 428/92 |
| 2005/0003980 A1 | 1/2005 | Baker et al. | |
| 2005/0025964 A1 | 2/2005 | Fairbanks et al. | |
| 2005/0026527 A1 | 2/2005 | Schmidt et al. | |
| 2005/0027270 A1 | 2/2005 | Cree et al. | |
| 2005/0087292 A1 | 4/2005 | Mcfall et al. | |
| 2005/0096614 A1 | 5/2005 | Perez et al. | |
| 2005/0131366 A1 | 6/2005 | Shimada | |
| 2005/0148971 A1 | 7/2005 | Kuroda et al. | |
| 2005/0175385 A1 | 8/2005 | Cho et al. | |
| 2005/0202208 A1 | 9/2005 | Kelly | |
| 2005/0228353 A1 * | 10/2005 | Thomas | A61F 13/537 604/385.01 |
| 2005/0233140 A1 | 10/2005 | Oh et al. | |
| 2005/0244619 A1 | 11/2005 | Kauschke et al. | |
| 2005/0256027 A1 | 11/2005 | Heibel et al. | |
| 2005/0256475 A1 | 11/2005 | Komatsu et al. | |
| 2005/0288647 A1 | 12/2005 | Ellingson et al. | |
| 2006/0019063 A1 | 1/2006 | Kelly | |
| 2006/0020251 A1 * | 1/2006 | Kelly | A61F 13/15203 604/378 |
| 2006/0068176 A1 | 3/2006 | Zafiroglu et al. | |
| 2006/0069361 A1 | 3/2006 | Olson | |
| 2006/0087053 A1 | 4/2006 | O'Donnell et al. | |
| 2006/0107505 A1 | 5/2006 | Desai et al. | |
| 2006/0113049 A1 * | 6/2006 | Knobloch | D21H 27/30 162/117 |
| 2006/0129114 A1 | 6/2006 | Mason et al. | |
| 2006/0135028 A1 | 6/2006 | Arendt et al. | |
| 2006/0135923 A1 | 6/2006 | Boggs et al. | |
| 2006/0141885 A1 | 6/2006 | Cobbs et al. | |
| 2006/0142710 A1 | 6/2006 | Kigata et al. | |
| 2006/0148358 A1 | 7/2006 | Hall et al. | |
| 2006/0179539 A1 | 8/2006 | Harber | |
| 2006/0252669 A1 | 11/2006 | Heibel et al. | |
| 2007/0015427 A1 | 1/2007 | Yanagawase et al. | |
| 2007/0021022 A1 | 1/2007 | Kishine et al. | |
| 2007/0032772 A1 | 2/2007 | Ehrnsperger et al. | |
| 2007/0036943 A1 | 2/2007 | Hirose et al. | |
| 2007/0048498 A1 | 3/2007 | Cree | |
| 2007/0073254 A1 | 3/2007 | Ponomarenko et al. | |
| 2007/0088307 A1 | 4/2007 | Arizti et al. | |
| 2007/0099817 A1 | 5/2007 | Smith et al. | |
| 2007/0135787 A1 | 6/2007 | Raidel et al. | |
| 2007/0191802 A1 | 8/2007 | Gubernick et al. | |
| 2007/0256286 A1 | 11/2007 | Ngai | |
| 2007/0275622 A1 | 11/2007 | Masuda et al. | |
| 2007/0275868 A1 | 11/2007 | Dykstra | |
| 2007/0293413 A1 | 12/2007 | McFarland et al. | |
| 2008/0076692 A1 | 3/2008 | Carvell et al. | |
| 2008/0138574 A1 | 6/2008 | Maschino et al. | |
| 2008/0143009 A1 | 6/2008 | Kurian et al. | |
| 2008/0249494 A1 | 10/2008 | Digiacomantonio et al. | |
| 2008/0294135 A1 | 11/2008 | Hara et al. | |
| 2008/0294138 A1 | 11/2008 | Andersson et al. | |
| 2008/0295256 A1 | 12/2008 | Broze et al. | |
| 2008/0300562 A1 | 12/2008 | Ahoniemi et al. | |
| 2008/0312343 A1 | 12/2008 | Braun et al. | |
| 2008/0312622 A1 | 12/2008 | Beruda et al. | |
| 2008/0317984 A1 | 12/2008 | Yamashita et al. | |
| 2009/0030390 A1 | 1/2009 | Hammons et al. | |
| 2009/0030391 A1 | 1/2009 | Hammons et al. | |
| 2009/0082746 A1 | 3/2009 | Thomas et al. | |
| 2009/0104831 A1 | 4/2009 | Bornemann et al. | |
| 2009/0124155 A1 | 5/2009 | Tiemeier et al. | |
| 2009/0131896 A1 | 5/2009 | Ebitsuka et al. | |
| 2009/0157021 A1 | 6/2009 | Sullivan et al. | |
| 2009/0191779 A1 | 7/2009 | Cree | |
| 2009/0233046 A1 | 9/2009 | Iulianetti | |
| 2009/0247978 A1 | 10/2009 | Boissier | |
| 2009/0259208 A1 | 10/2009 | Hellstrom et al. | |
| 2009/0299316 A1 | 12/2009 | Seyler | |
| 2009/0318050 A1 | 12/2009 | Okaya | |
| 2010/0004615 A1 | 1/2010 | Boissier | |
| 2010/0019415 A1 | 1/2010 | Stone et al. | |
| 2010/0035014 A1 | 2/2010 | Hammons et al. | |

(56) References Cited

U.S. PATENT DOCUMENTS

| | | |
|---|---|---|
| 2010/0036338 A1 | 2/2010 | Hammons et al. |
| 2010/0036346 A1 | 2/2010 | Hammons et al. |
| 2010/0100067 A1 | 4/2010 | Pugliese, III |
| 2010/0105273 A1 | 4/2010 | Motomura et al. |
| 2010/0107396 A1 | 5/2010 | Yagyu et al. |
| 2010/0130952 A1 | 5/2010 | Murai |
| 2010/0159770 A1 | 6/2010 | Walser et al. |
| 2010/0164733 A1 | 7/2010 | Ales et al. |
| 2010/0190679 A1 | 7/2010 | Vanpachtenbeke et al. |
| 2010/0196653 A1 | 8/2010 | Curro et al. |
| 2010/0227130 A1 | 9/2010 | Takahashi |
| 2010/0233438 A1 | 9/2010 | Stone et al. |
| 2010/0252138 A1 | 10/2010 | Tseng |
| 2010/0261399 A1 | 10/2010 | Katsuya et al. |
| 2010/0280471 A1 | 11/2010 | Shah |
| 2010/0330326 A1 | 12/2010 | Turner et al. |
| 2011/0004176 A1* | 1/2011 | Andersson .......... A61F 13/5146 604/378 |
| 2011/0024940 A1 | 2/2011 | Khalid et al. |
| 2011/0046592 A1 | 2/2011 | Nishikawa et al. |
| 2011/0073513 A1 | 3/2011 | Weisman et al. |
| 2011/0106036 A1 | 5/2011 | Staahl et al. |
| 2011/0117307 A1 | 5/2011 | Fraser et al. |
| 2011/0184370 A1 | 7/2011 | Seyler et al. |
| 2011/0189915 A1 | 8/2011 | Morimoto et al. |
| 2011/0196330 A1 | 8/2011 | Hammons et al. |
| 2011/0236683 A1 | 9/2011 | Takebe et al. |
| 2011/0245141 A1 | 10/2011 | Gizaw et al. |
| 2011/0264064 A1 | 10/2011 | Arora et al. |
| 2011/0269663 A1 | 11/2011 | Clowes et al. |
| 2011/0301312 A1 | 12/2011 | Blondel |
| 2011/0305870 A1 | 12/2011 | Curro et al. |
| 2011/0313385 A1 | 12/2011 | Hammons et al. |
| 2011/0319853 A1 | 12/2011 | Yamashita et al. |
| 2012/0003423 A1 | 1/2012 | Cree et al. |
| 2012/0035566 A1 | 2/2012 | Sagisaka et al. |
| 2012/0043036 A1* | 2/2012 | Polat .................. D21H 27/02 162/116 |
| 2012/0095426 A1 | 4/2012 | Visscher et al. |
| 2012/0121882 A1 | 5/2012 | Okaya |
| 2012/0171913 A1 | 7/2012 | Fox et al. |
| 2012/0177886 A1 | 7/2012 | Kanya et al. |
| 2012/0273990 A1 | 11/2012 | O'Donnell et al. |
| 2012/0282436 A1 | 11/2012 | Coe et al. |
| 2012/0289917 A1 | 11/2012 | Abuto et al. |
| 2012/0295060 A1 | 11/2012 | Mullane |
| 2012/0296304 A1 | 11/2012 | Choo et al. |
| 2013/0012898 A1 | 1/2013 | Bergendahl et al. |
| 2013/0029555 A1 | 1/2013 | Morimoto |
| 2013/0097101 A1 | 4/2013 | Ortiz |
| 2013/0109612 A1 | 5/2013 | Corona, III et al. |
| 2013/0121944 A1 | 5/2013 | Leyrer et al. |
| 2013/0121945 A1 | 5/2013 | Leyrer et al. |
| 2013/0129657 A1 | 5/2013 | Streuli |
| 2013/0139666 A1 | 6/2013 | Raidel et al. |
| 2013/0226122 A1 | 8/2013 | Roe et al. |
| 2013/0253461 A1 | 9/2013 | Xu et al. |
| 2013/0310300 A1 | 11/2013 | Leyrer et al. |
| 2013/0310301 A1 | 11/2013 | Sivik et al. |
| 2014/0029815 A1 | 1/2014 | Kadir et al. |
| 2014/0031779 A1 | 1/2014 | Hammons et al. |
| 2014/0033605 A1 | 2/2014 | Sondjaja et al. |
| 2014/0044934 A1 | 2/2014 | Bills et al. |
| 2014/0047649 A1 | 2/2014 | Blondel |
| 2014/0066873 A1 | 3/2014 | Kawakami et al. |
| 2014/0087130 A1 | 3/2014 | Seyler et al. |
| 2014/0121624 A1 | 5/2014 | Kirby et al. |
| 2014/0148773 A1 | 5/2014 | Brown et al. |
| 2014/0148774 A1 | 5/2014 | Brown et al. |
| 2014/0151934 A1 | 6/2014 | Thomas et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0228795 A1 | 8/2014 | Castanares et al. |
| 2014/0296809 A1 | 10/2014 | Hammons et al. |
| 2014/0296815 A1 | 10/2014 | Takken et al. |
| 2014/0303581 A1 | 10/2014 | Karlsson |
| 2014/0315779 A1 | 10/2014 | Zander |
| 2014/0324009 A1 | 10/2014 | Lee et al. |
| 2014/0336605 A1 | 11/2014 | Hardie et al. |
| 2014/0378639 A1 | 12/2014 | Blondel et al. |
| 2015/0099086 A1 | 4/2015 | Kim et al. |
| 2015/0191677 A1 | 7/2015 | Blondel |
| 2015/0197708 A1 | 7/2015 | Jin |
| 2015/0209189 A1 | 7/2015 | Mullane |
| 2015/0250663 A1 | 9/2015 | Wagner et al. |
| 2015/0283001 A1 | 10/2015 | Arizti et al. |
| 2015/0283003 A1 | 10/2015 | Rosati et al. |
| 2015/0329799 A1 | 11/2015 | Schramm, Jr. et al. |
| 2015/0337239 A1 | 11/2015 | Gonzalez de Cossio et al. |
| 2016/0024426 A1 | 1/2016 | Sivik et al. |
| 2016/0024427 A1 | 1/2016 | Sivik et al. |
| 2016/0024428 A1 | 1/2016 | Dykstra et al. |
| 2016/0024429 A1 | 1/2016 | Dykstra et al. |
| 2016/0024430 A1 | 1/2016 | Dykstra et al. |
| 2016/0024431 A1 | 1/2016 | Dykstra et al. |
| 2016/0024432 A1 | 1/2016 | Sivik et al. |
| 2016/0024434 A1 | 1/2016 | Sivik et al. |
| 2016/0032220 A1 | 2/2016 | Sivik et al. |
| 2016/0113826 A1 | 4/2016 | Liu et al. |
| 2016/0129626 A1 | 5/2016 | Arora et al. |
| 2016/0136003 A1 | 5/2016 | Mullane et al. |
| 2016/0136010 A1 | 5/2016 | Roe et al. |
| 2016/0136014 A1 | 5/2016 | Arora et al. |
| 2016/0136015 A1 | 5/2016 | Giovanni et al. |
| 2016/0136016 A1 | 5/2016 | Mullane et al. |
| 2016/0136919 A1 | 5/2016 | Roe et al. |
| 2017/0151103 A1 | 6/2017 | Bianchi et al. |
| 2017/0175313 A1* | 6/2017 | Song ..................... A61F 13/511 |
| 2018/0000654 A1 | 1/2018 | Arora et al. |
| 2018/0000655 A1 | 1/2018 | Mullane et al. |
| 2018/0000656 A1 | 1/2018 | Roe et al. |
| 2018/0228660 A1 | 8/2018 | Mullane et al. |
| 2018/0235817 A1 | 8/2018 | Mullane et al. |
| 2018/0318144 A1 | 11/2018 | Giovanni et al. |
| 2019/0240082 A1 | 8/2019 | Mullane et al. |
| 2019/0290503 A1 | 9/2019 | Mullane et al. |
| 2020/0246199 A1 | 8/2020 | Mullane et al. |

FOREIGN PATENT DOCUMENTS

| | | |
|---|---|---|
| CA | 2733472 | 9/2009 |
| CA | 2482306 C | 10/2011 |
| CN | 1207662 A | 2/1999 |
| CN | 2331362 A | 8/1999 |
| CN | 1290156 A | 4/2001 |
| CN | 2567250 Y | 8/2003 |
| CN | 1575787 A | 2/2005 |
| CN | 1772984 A | 5/2006 |
| CN | 1901862 A | 1/2007 |
| CN | 2897211 | 5/2007 |
| CN | 202724134 U | 11/2009 |
| CN | 201505226 | 6/2010 |
| CN | 101790606 A | 7/2010 |
| CN | 201618014 | 11/2010 |
| CN | 201855363 | 6/2011 |
| CN | 101724132 B | 11/2011 |
| CN | 102673030 | 9/2012 |
| CN | 101940514 B | 12/2013 |
| CN | 103747955 A | 4/2014 |
| CN | 103842570 A | 6/2014 |
| DE | 2806401 | 8/1979 |
| DE | 4106295 | 9/1992 |
| DE | 19647459 | 5/1998 |
| DE | 19846857 | 3/2000 |
| EP | 165807 | 12/1985 |
| EP | 0172025 A2 | 2/1986 |
| EP | 0172723 A2 | 2/1986 |
| EP | 0172724 A2 | 2/1986 |
| EP | 0330212 A2 | 8/1989 |
| EP | 0343840 A2 | 11/1989 |
| EP | 359501 | 3/1990 |
| EP | 495212 | 7/1992 |
| EP | 535579 | 4/1993 |

(56) References Cited

FOREIGN PATENT DOCUMENTS

| | | |
|---|---|---|
| EP | 545423 | 6/1993 |
| EP | 0212284 B1 | 9/1993 |
| EP | 0589224 | 3/1994 |
| EP | 0691427 A1 | 1/1996 |
| EP | 0696655 A1 | 2/1996 |
| EP | 749736 | 12/1996 |
| EP | 749737 | 12/1996 |
| EP | 749738 | 12/1996 |
| EP | 749739 | 12/1996 |
| EP | 749740 | 12/1996 |
| EP | 0761846 A2 | 3/1997 |
| EP | 0934737 | 8/1999 |
| EP | 983758 | 3/2000 |
| EP | 1022007 | 7/2000 |
| EP | 1040807 | 10/2000 |
| EP | 1084689 A2 | 3/2001 |
| EP | 1086676 | 3/2001 |
| EP | 0710472 | 4/2001 |
| EP | 1290995 A2 | 3/2003 |
| EP | 1066006 | 5/2003 |
| EP | 1352948 A1 | 10/2003 |
| EP | 1140228 | 3/2004 |
| EP | 1625195 B1 | 5/2007 |
| EP | 1740682 B1 | 6/2009 |
| EP | 1756168 B1 | 7/2009 |
| EP | 2110472 A1 | 10/2009 |
| EP | 2284250 A1 | 2/2011 |
| EP | 2347872 | 7/2011 |
| EP | 1781717 B1 | 11/2012 |
| EP | 1988793 B1 | 7/2014 |
| FR | 2862975 B1 | 2/2006 |
| GB | 2002400 A | 2/1979 |
| GB | 2103933 | 3/1983 |
| GB | 2225724 | 6/1990 |
| GB | 2296464 | 7/1996 |
| GB | 2310606 | 9/1997 |
| JP | 03186261 | 8/1991 |
| JP | H04327211 A | 11/1992 |
| JP | H04327256 A | 11/1992 |
| JP | H05195406 A | 8/1993 |
| JP | 6038818 | 2/1994 |
| JP | 06280150 | 10/1994 |
| JP | H07216653 A | 8/1995 |
| JP | 2587116 | 3/1997 |
| JP | H0959823 A | 3/1997 |
| JP | H09310226 A | 12/1997 |
| JP | 10272152 | 10/1998 |
| JP | 2790875 | 12/1998 |
| JP | H11152624 A | 6/1999 |
| JP | 2001032139 A | 2/2001 |
| JP | 2002180331 A | 6/2002 |
| JP | 2003003334 A | 1/2003 |
| JP | 2003275238 A | 9/2003 |
| JP | 2004041870 A | 2/2004 |
| JP | 2004187810 A | 7/2004 |
| JP | 2004154250 A | 8/2004 |
| JP | 2005040235 A | 2/2005 |
| JP | 2005200795 A | 7/2005 |
| JP | 2005245789 A | 9/2005 |
| JP | 2008006272 A | 1/2008 |
| JP | 2008127705 A | 6/2008 |
| JP | 2008174880 A | 7/2008 |
| JP | 2008179939 A | 8/2008 |
| JP | 2009050621 | 3/2009 |
| JP | 2009172354 | 8/2009 |
| JP | 2010051697 A * | 3/2010 |
| JP | 2010269029 | 12/2010 |
| JP | 2011078477 A | 4/2011 |
| JP | 2011135979 | 7/2011 |
| JP | 2011239835 | 12/2011 |
| JP | 2012050548 | 3/2012 |
| JP | 2012154010 A | 8/2012 |
| JP | 2012158547 A | 8/2012 |
| JP | 5034078 B2 | 9/2012 |
| JP | 2013011051 A | 1/2013 |
| JP | 4357591 | 2/2013 |
| JP | 2014034741 A | 2/2014 |
| JP | 2014097240 A | 5/2014 |
| JP | 2014511739 A | 5/2014 |
| JP | 5528660 B2 | 6/2014 |
| JP | 3209591 B2 | 3/2017 |
| KR | 2001064584 | 7/2001 |
| KR | 20010064584 A * | 7/2001 |
| KR | 20030089593 A | 11/2003 |
| KR | 20140006704 A | 1/2014 |
| KR | 20150100549 A | 9/2015 |
| WO | 9003464 A2 | 4/1990 |
| WO | WO 91/10415 | 7/1991 |
| WO | WO 93/11726 | 6/1993 |
| WO | WO 93/15701 | 8/1993 |
| WO | WO 95/13773 | 5/1995 |
| WO | WO 95/17867 | 7/1995 |
| WO | 9607689 A1 | 3/1996 |
| WO | WO 96/10481 | 4/1996 |
| WO | WO 96/11107 | 4/1996 |
| WO | WO 96/19313 | 6/1996 |
| WO | 9621759 A1 | 7/1996 |
| WO | WO 97/02133 | 1/1997 |
| WO | WO 2007/01320 | 1/1997 |
| WO | WO 97/03818 | 2/1997 |
| WO | WO1997/09020 | 3/1997 |
| WO | WO1997/11661 | 4/1997 |
| WO | 9853896 A1 | 12/1998 |
| WO | 9920725 A1 | 4/1999 |
| WO | WO 9930660 | 6/1999 |
| WO | WO 9939671 | 8/1999 |
| WO | 9960975 A1 | 12/1999 |
| WO | WO 2000/001334 | 1/2000 |
| WO | WO 2000/028929 | 5/2000 |
| WO | WO 2000/037249 | 6/2000 |
| WO | WO 2000/062826 | 10/2000 |
| WO | WO 2001/072251 | 10/2001 |
| WO | WO 2002/100632 | 12/2002 |
| WO | WO 2003/015681 | 2/2003 |
| WO | WO 03024706 | 3/2003 |
| WO | WO 2003/071019 | 8/2003 |
| WO | 03102043 A | 12/2003 |
| WO | WO 2004/009009 | 1/2004 |
| WO | 2004050812 A1 | 6/2004 |
| WO | 2004058497 A1 | 7/2004 |
| WO | WO 2004/098474 | 11/2004 |
| WO | 2005087907 A1 | 9/2005 |
| WO | 2005097834 A2 | 10/2005 |
| WO | 2007116346 A1 | 10/2007 |
| WO | 2008005693 A2 | 1/2008 |
| WO | 2010141309 A1 | 12/2010 |
| WO | WO 2011/080643 | 7/2011 |
| WO | WO 2012/14957 | 2/2012 |
| WO | WO 2012/052172 | 4/2012 |
| WO | 2012076432 A1 | 6/2012 |
| WO | 2013068388 A1 | 5/2013 |
| WO | 2013068394 A1 | 5/2013 |
| WO | WO 2013/91150 | 6/2013 |
| WO | 2013142486 A1 | 9/2013 |
| WO | 2013163360 A2 | 10/2013 |
| WO | 2013163388 A1 | 10/2013 |
| WO | WO 2013/147222 | 10/2013 |
| WO | 2014022652 A1 | 2/2014 |
| WO | 2014108106 A1 | 7/2014 |
| WO | 2015130088 A1 | 9/2015 |
| WO | 2017082834 A1 | 5/2017 |

OTHER PUBLICATIONS

Pad Size Chart, Apr. 2015 (Year: 2015).*
International Search Report and Written Opinion, PCT/US2018/018280, dated Apr. 13, 2018.
All Office Actions, U.S. Appl. No. 15/897,184.
All Office Actions, U.S. Appl. No. 14/933,013.
All Office Actions, U.S. Appl. No. 14/933,015.
All Office Actions, U.S. Appl. No. 14/933,021.
All Office Actions, U.S. Appl. No. 16/032,117.
All Office Actions, U.S. Appl. No. 14/933,024.

(56) References Cited

OTHER PUBLICATIONS

All Office Actions, U.S. Appl. No. 15/704,027.
All Office Actions, U.S. Appl. No. 14/933,030.
All Office Actions, U.S. Appl. No. 15/704,030.
All Office Actions, U.S. Appl. No. 15/953,586.
All Office Actions, U.S. Appl. No. 15/953,742.
All Office Actions, U.S. Appl. No. 16/386,632.
All Office Actions, U.S. Appl. No. 16/432,084.
All Office Actions, U.S. Appl. No. 14/933,034.
All Office Actions, U.S. Appl. No. 15/704,035.
All Office Actions, U.S. Appl. No. 14/933,039.
Amimasr E., "Analysis of Basis Weight Uniformity of Microfiber Nonwovens and Its Impact on Permeability and Filtration Properties," North Carolina State University, 2012, retrieved from the Internet URL https://repositoryJib.ncsu.edu/handle/1840.16/9096, 294 pages.
Analyze Menu, retrieved from the Internet URL "https://imagej.nih.gov/ij/docs/menus/analyze.html", retrieved on Dec. 19, 2021, 12 pages.
ASTM D3954-94 (Reapproved 2010), "Standard Test Method for Dropping Point of Waxes," D3954-94 (2010), 2 pages.
Auto Threshold—ImageJ, http://imagej.netlAuto_Threshold, last modified on Dec. 15, 2017, 7 pages.
Ferreira, T. and Rasband W., "ImageJ User Guide," IJ 1.46r, Retrieved from the Internet URL https://imagej.nih.gov/i/docs/guide/user-guide.pdf. Last modified Sep./Oct. 2012, p. 79.
Morphological Image Processing, Retrieved from the Internet URL https://www.cs.auckland.ac.nz/courses/compsci773slc/lectures/ImageProcessing-html/topic4.htm#erosion, retrieved on Apr. 19, 2021, 7 pages.
Process Menu, retrieved from the Internet URL "https://imagej.nih.gov/ij/docs/menus/process.html", retrieved on Dec. 19, 2021, 17 pages.
Schuck, P. "Size-Distribution Analysis of Macromolecules by Sedimentation Velocity Ultracentrifugation and Lamm Equation Modeling," Biophysical Journal, vol. 78, Mar. 2000, pp. 1606-1619.
All Office Actions; U.S. Appl. No. 17/361,681.
U.S. Appl. No. 17/361,681, filed Jun. 29, 2021, to Timothy Ian Mullane et al.

* cited by examiner

SUBSTRATES HAVING REPEATING PATTERNS OF APERTURES FOR ABSORBENT ARTICLES

CROSS REFERENCE TO RELATED APPLICATIONS

This application is a continuation of, and claims priority under 35 U.S.C. § 120 to, U.S. patent application Ser. No. 15/897,184, filed on Feb. 15, 2018, which claims the benefit, under 35 U.S.C. § 119(e), of U.S. Provisional Patent Application Ser. No. 62/459,765, filed on Feb. 16, 2017, the entire disclosures of which are fully incorporated by reference herein.

FIELD

The present disclosure is directed generally to substrates or topsheets having repeating patterns of apertures for absorbent articles.

BACKGROUND

Absorbent articles are used to absorb and contain bodily exudates (e.g., urine, menses, and BM) in infants, children, and adults. Absorbent articles may comprise diapers, pants, adult incontinence products, and sanitary napkins, for example. The absorbent articles typically comprise a liquid permeable topsheet, a liquid impermeable backsheet, and an absorbent core disposed at least partially the topsheet and the backsheet. Apertures may be formed in the topsheet to allow bodily exudate penetration through the topsheet. Apertures are sometimes present in a topsheet in a uniform manner (e.g., a one size, one shape aperture that is repeated throughout the topsheet with uniform spacing between the apertures). Topsheets with uniform aperture patterns may not be desired because they do not look customized. If apertures were to be presented in patterns, bodily exudate penetration becomes more complicated owing to the non-uniform nature of the topsheets. What is needed are absorbent article topsheets comprising repeating patterns of apertures comprising a plurality of repeat unit that perform parity to or better than topsheets with uniform aperture patterns with respect to penetration, absorbency, softness, run-off, and rewet.

SUMMARY

The present disclosure provides absorbent article with substrates or topsheets having repeating patterns of apertures comprising a plurality of repeat units that perform parity to or better than uniform aperture patterns and that also provide consumers with a more fanciful topsheet that is aesthetically appealing. The substrates or topsheets with repeating patterns of apertures comprising a plurality of repeat units perform parity to or better than topsheets with uniform aperture patterns with respect to penetration, absorbency, softness, run-off, and rewet. Repeating patterns of apertures comprising a plurality of repeat units may further provide signals of multiple functions, such as larger apertures for absorbency and smaller apertures for breathability. For sufficient bodily exudate acquisition and to minimize bodily exudate run-off and leakage, it may be desirable to have a minimum size for the apertures in the repeat units and have certain effective open areas in the topsheets to allow the bodily exudates to penetrate the topsheet and be absorbed by the hydrophilic layers underneath the topsheet (e.g., an acquisition layer or an absorbent core). Effective open areas in the topsheets that are too high, however, may lead to higher rewet and reduced softness of the topsheets. As such, desirable effective open areas in the range of 5% to 50%, 5% to 30%, or 5% to 15% may provide a good balance of softness and absorbency. When repeating patterns of apertures comprising a plurality of repeat units (compared to uniform apertures throughout) are utilized in topsheets to enhance visual aesthetics and perception of performance, the same technical requirements apply. At the same effective open area ranges of a uniform apertured topsheet, a topsheet with the repeating pattern of apertures comprising a plurality of repeat units may provide a topsheet that is not only visually appealing, but also efficacious. If the individual repeat units are too small (e.g., too many repeat units across a lateral width or longitudinal length of an absorbent article), the apertures, by necessity, will also be smaller than desired for bodily exudate handling. On the other hand, if the individual repeat units are too large, or are surrounded by too much land area (e.g., only one or one and a half repeat units across an absorbent article width), the bodily exudates may only be absorbed into the repeat unit area having apertures and not into surrounding land areas of the repeat units that are free of apertures and the absorbent article may not perform as well.

The present disclosure is directed, in part, to an absorbent article comprising a central lateral axis, a central longitudinal axis extending perpendicular to the central lateral axis, a liquid permeable apertured topsheet, a liquid impermeable backsheet, and an absorbent core disposed at least partially intermediate the topsheet and the backsheet. The absorbent core may comprise an absorbent material that is substantially free of air-felt or free of air-felt. The absorbent article has a total length along the central longitudinal axis, as measured according to the Repeat Unit Measurement Test. The absorbent article has a total width along the central lateral axis, as measured according to the Repeat Unit Measurement Test. The apertured topsheet comprises a repeating pattern of apertures comprising a plurality of repeat units. Each of the repeat units is the same or substantially the same. The repeat units repeat between about 3 and about 7 times along the total width, as measured by the Repeat Unit Measurement Test herein. At least a majority of the repeat units have a repeat unit area in the range of about 200 mm$^2$ to about 1500 mm$^2$ or about 900 mm$^2$ to about 1500 mm$^2$.

BRIEF DESCRIPTION OF THE DRAWINGS

While the specification concludes with claims particularly pointing out and distinctly claiming the subject matter which is regarded as forming the present invention, it is believed that the present disclosure will be better understood from the following description which is taken in conjunction with the accompanying drawings in which the designations are used to designate substantially identical elements and in which:

FIG. 22 is a schematic illustration of a portion of a topsheet comprising a repeating pattern of apertures comprising a plurality of repeat unit, wherein the repeat units are substantially similar;

FIG. 23 is a schematic illustration of a portion of a topsheet comprising a repeating pattern of apertures comprising a plurality of repeat unit, wherein the repeat units are substantially similar;

DETAILED DESCRIPTION

Figure 1:
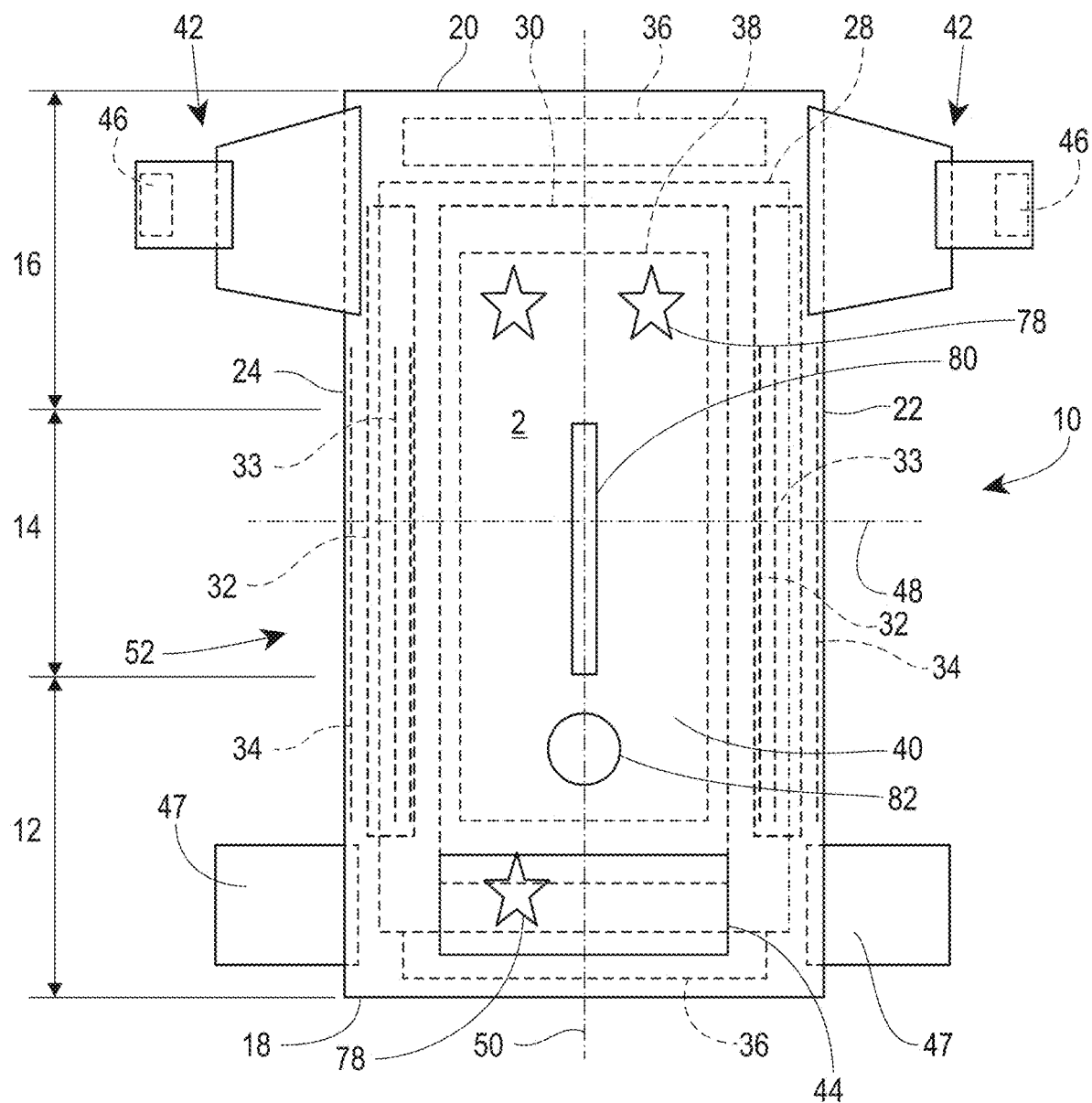
FIG. 1 is a plan view of an example absorbent article in the form of a taped diaper, garment-facing surface facing the viewer, in a flat laid-out state.

Various non-limiting forms of the present disclosure will now be described to provide an overall understanding of the principles of the structure, function, manufacture, and use of the substrates having repeating patterns of apertures for absorbent articles disclosed herein. One or more examples of these non-limiting forms are illustrated in the accompanying drawings. Those of ordinary skill in the art will understand that the substrates having repeating patterns of apertures for absorbent articles specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the term "absorbent article", refers to devices which absorb and contain bodily exudates (e.g., BM, urine, menses), and, more specifically, refers to devices which are placed against or in proximity to the body of the wearer to absorb and contain the various bodily exudates discharged from the body. The term absorbent article includes, but is not limited to, diapers, pants, training pants, adult incontinence products, and sanitary napkins, and liners. The term "absorbent article" may also encompass cleaning or dusting pads or substrates that have some absorbency.

As used herein, the terms "join", "joined", "joining", "bond", "bonded", "bonding", "attach", "attached", or "attaching" encompass configurations whereby an element is directly secured to another element by affixing the element directly to the other element, and configurations whereby an element is indirectly secured to another element by affixing the element to intermediate member(s) which in turn are affixed to the other element.

As used herein, the term "nanofibers", refers to very small diameter fibers having an average diameter less than about 1 micron.

As used herein, the term "meltblown", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carded by the high velocity gas stream and are deposited on a collecting surface to form a web of randomly dispersed meltblown fibers.

As used herein, the term "spunbond", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

Example absorbent articles designs that may contain substrates or topsheets with repeating patterns of apertures comprising a plurality of repeat units are first discussed below. The substrates may be topsheets, outer cover nonwoven materials, or other substrates of absorbent articles.

General Description of an Absorbent Article

Figure 2:
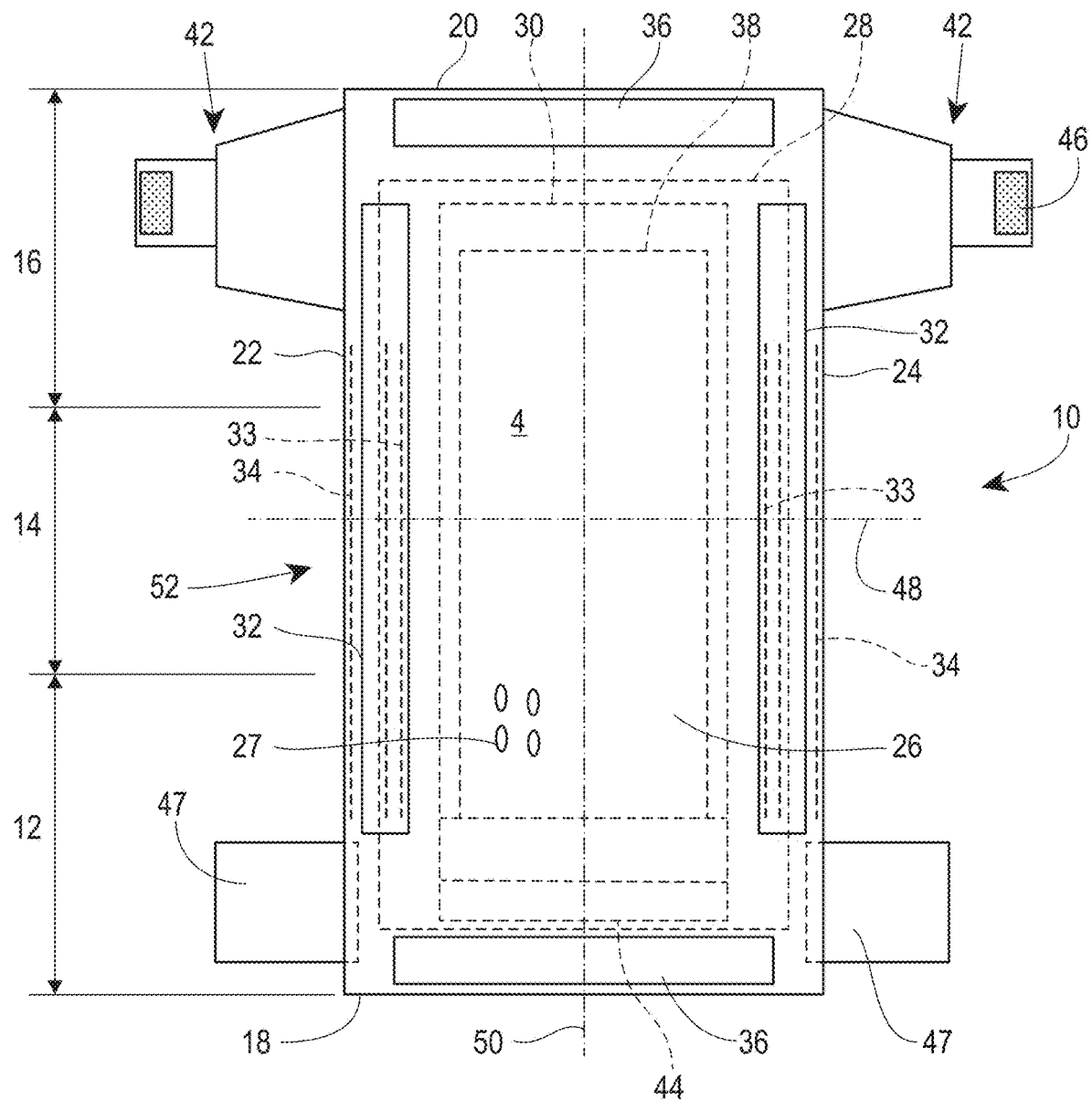
FIG. 2 is a plan view of the example absorbent article of FIG. 1, wearer-facing surface facing the viewer, in a flat laid-out state.
Figure 3:
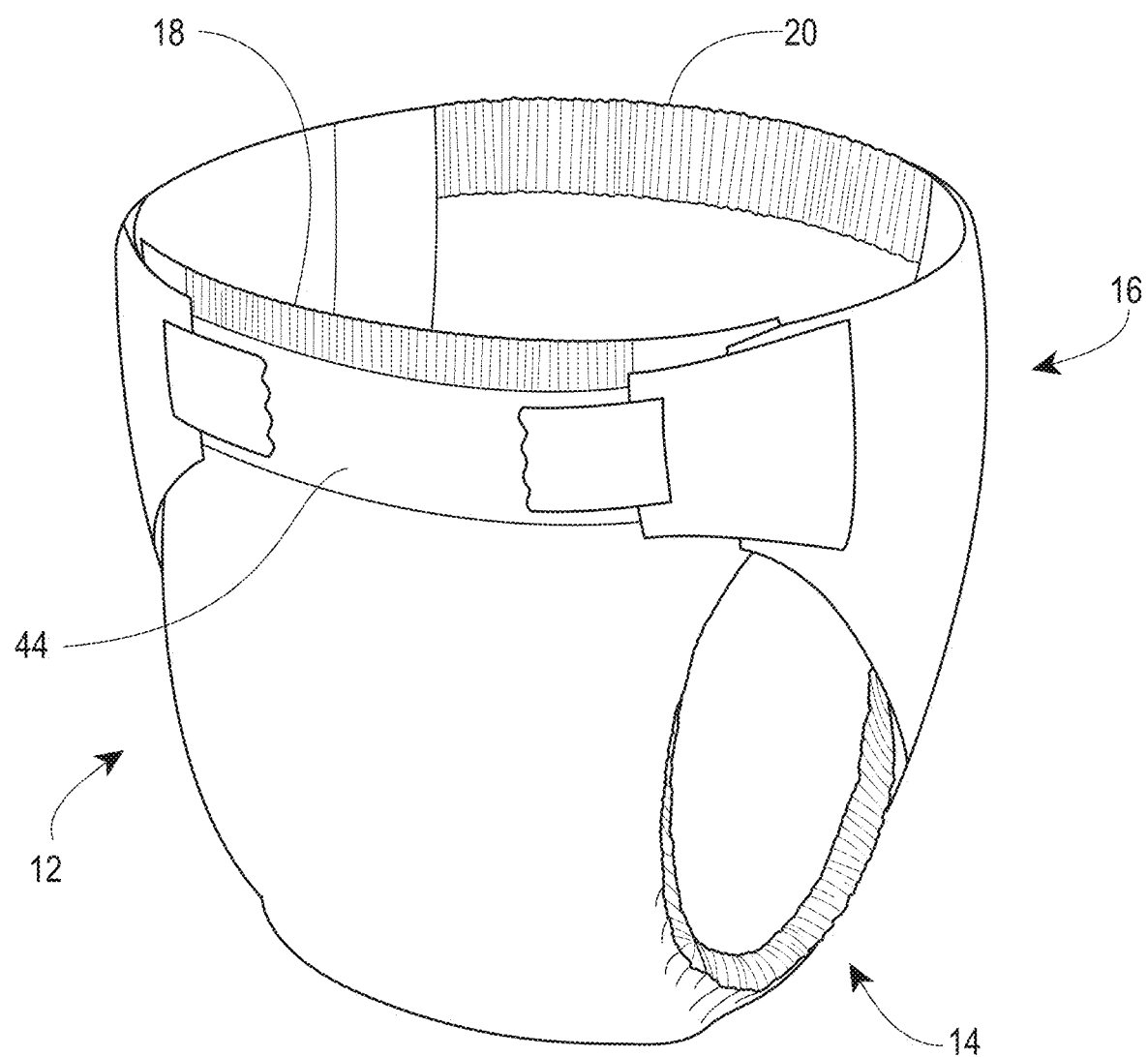
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
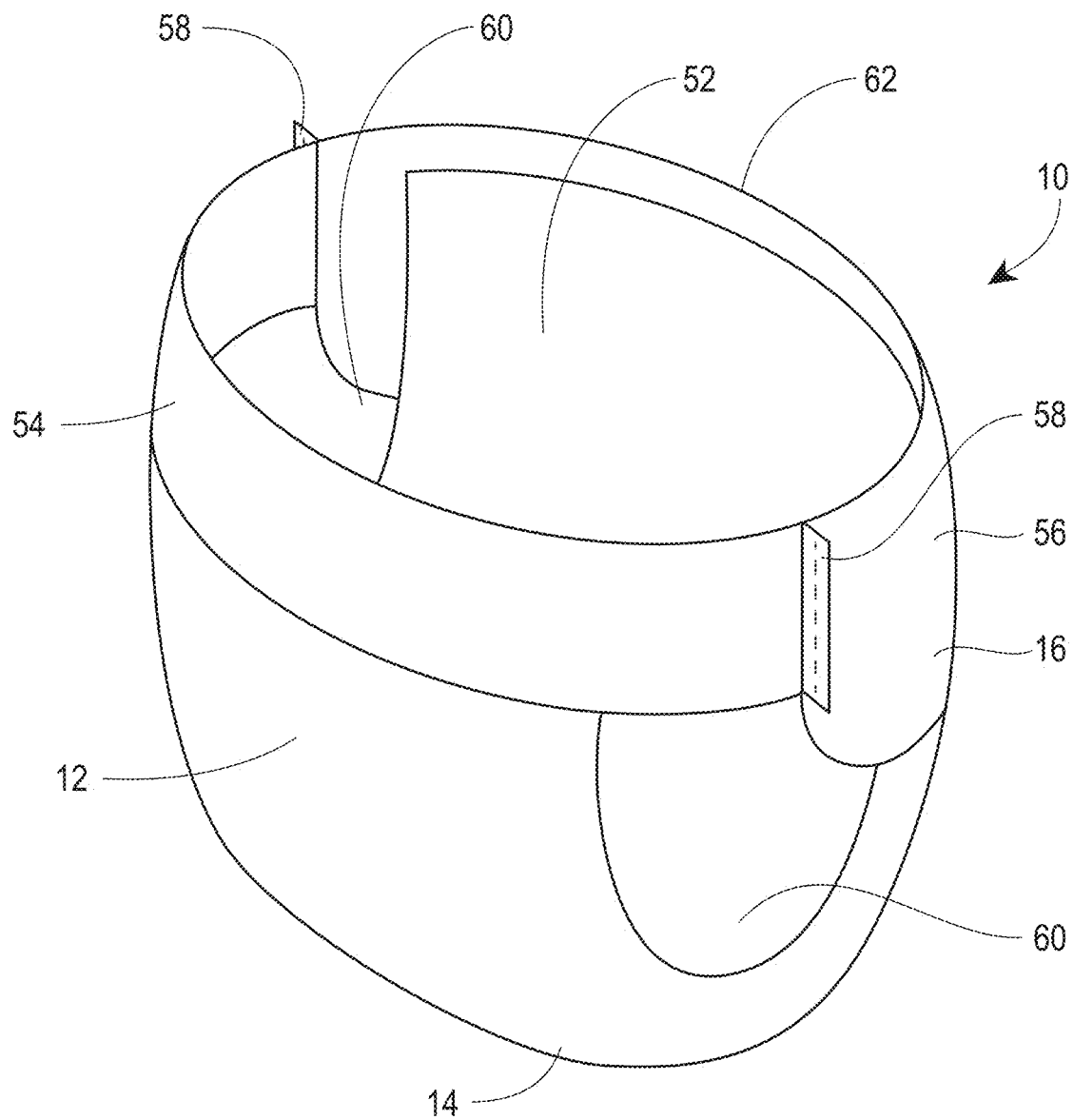
FIG. 4 is a front perspective view of an absorbent article in the form of a pant.
Figure 5:
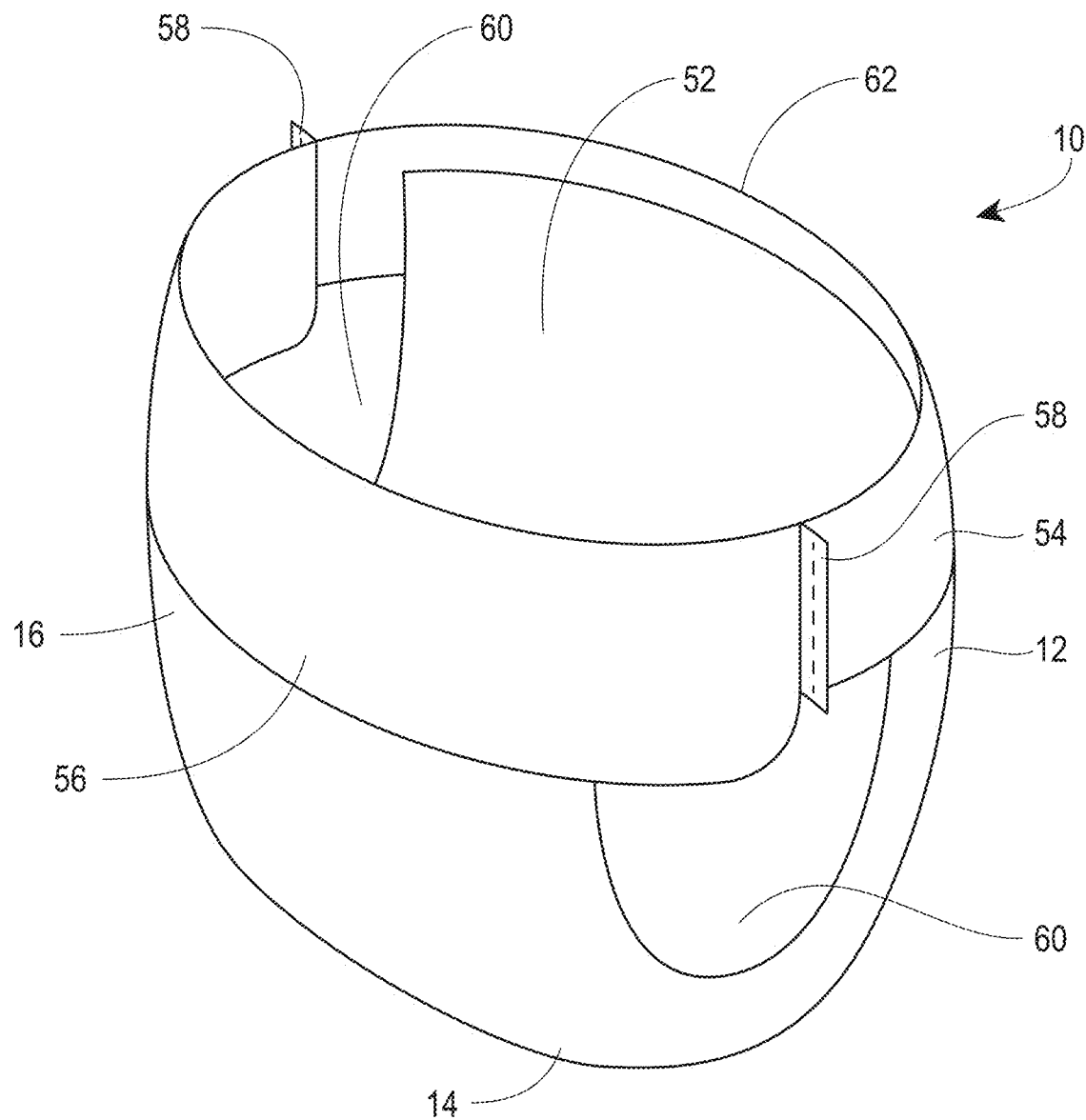
FIG. 5 is a rear perspective view of the absorbent article of FIG. 4.
Figure 6:
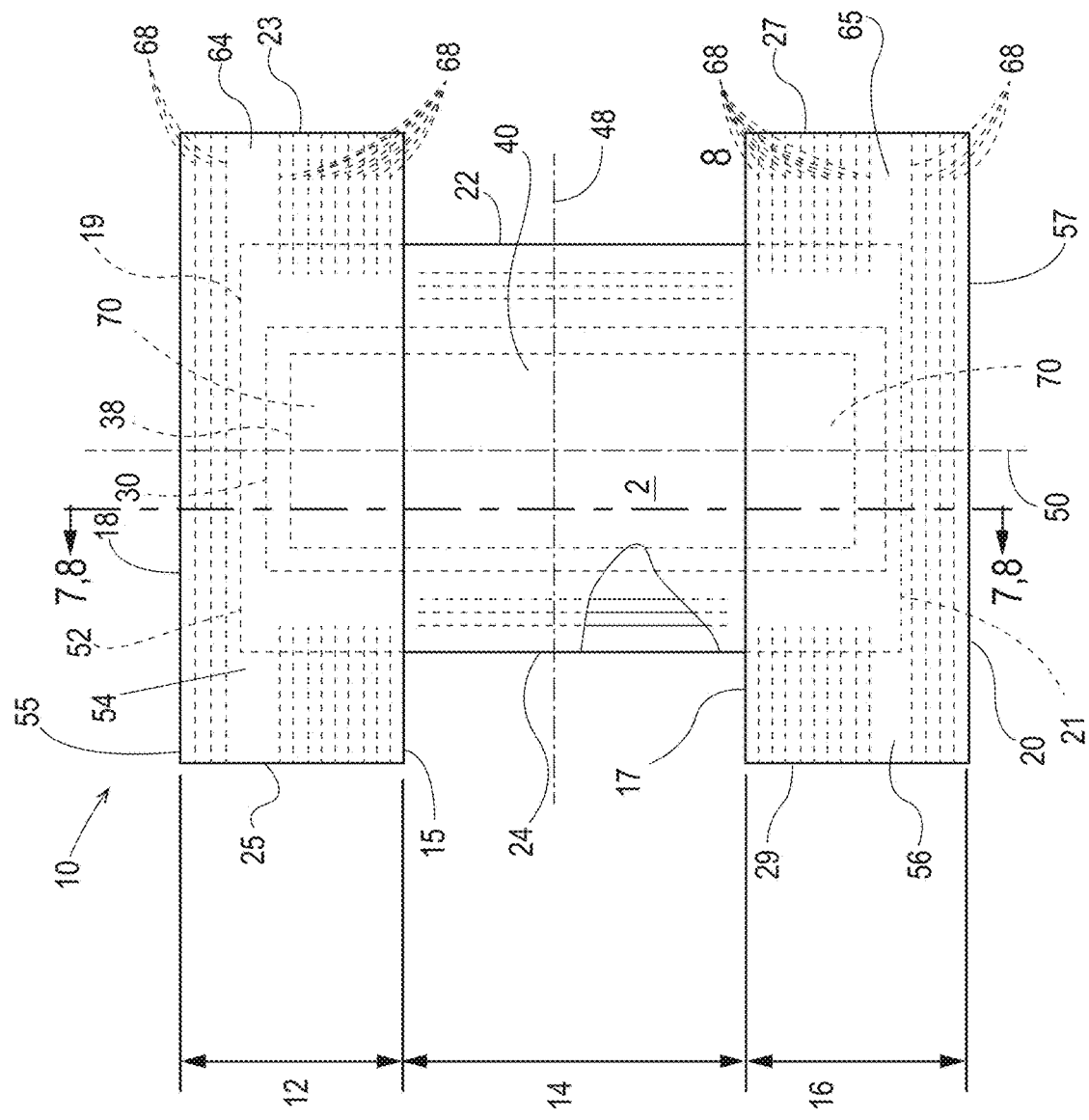
FIG. 6 is a plan view of the absorbent article of FIG. 4, laid flat, with a garment-facing surface facing the viewer.
Figure 7:
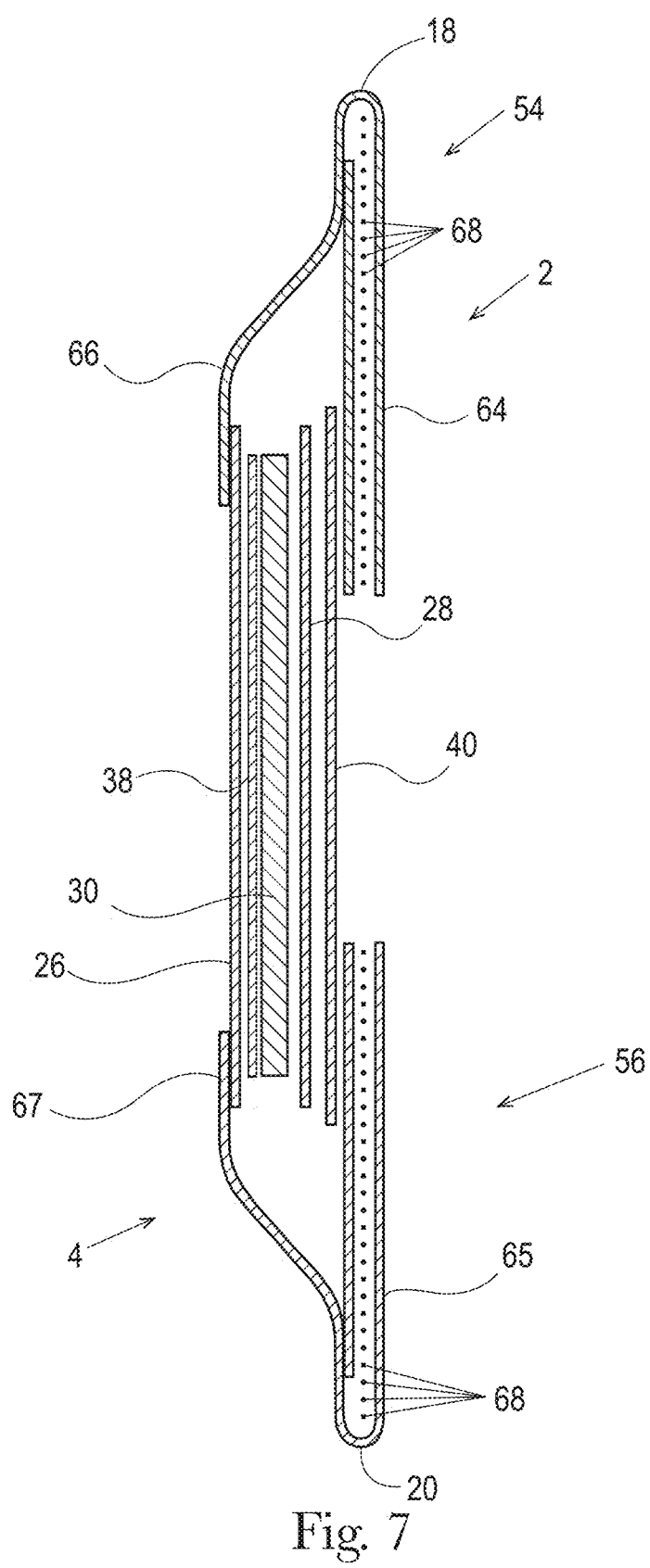
FIG. 7 is a cross-sectional view of the absorbent article taken about line 7-7 of FIG. 6.
Figure 8:
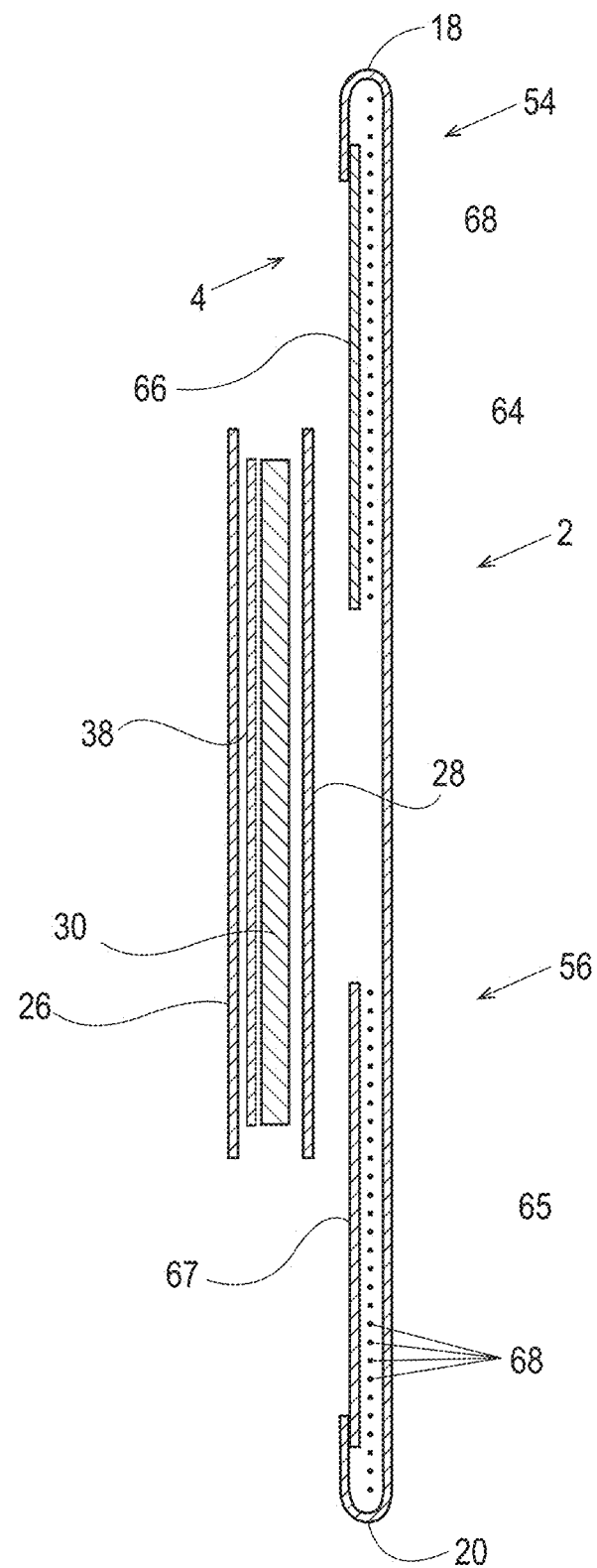
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. Some topsheets may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (e.g., FIG. 2, element 27), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. Repeating patterns of apertures comprising a plurality of repeat units in the topsheets will be discussed in greater detail below.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features. The outer cover material 40 may have the repeating patterns of apertures comprising the plurality of repeat units discussed herein.

Absorbent Core

Figure 9:
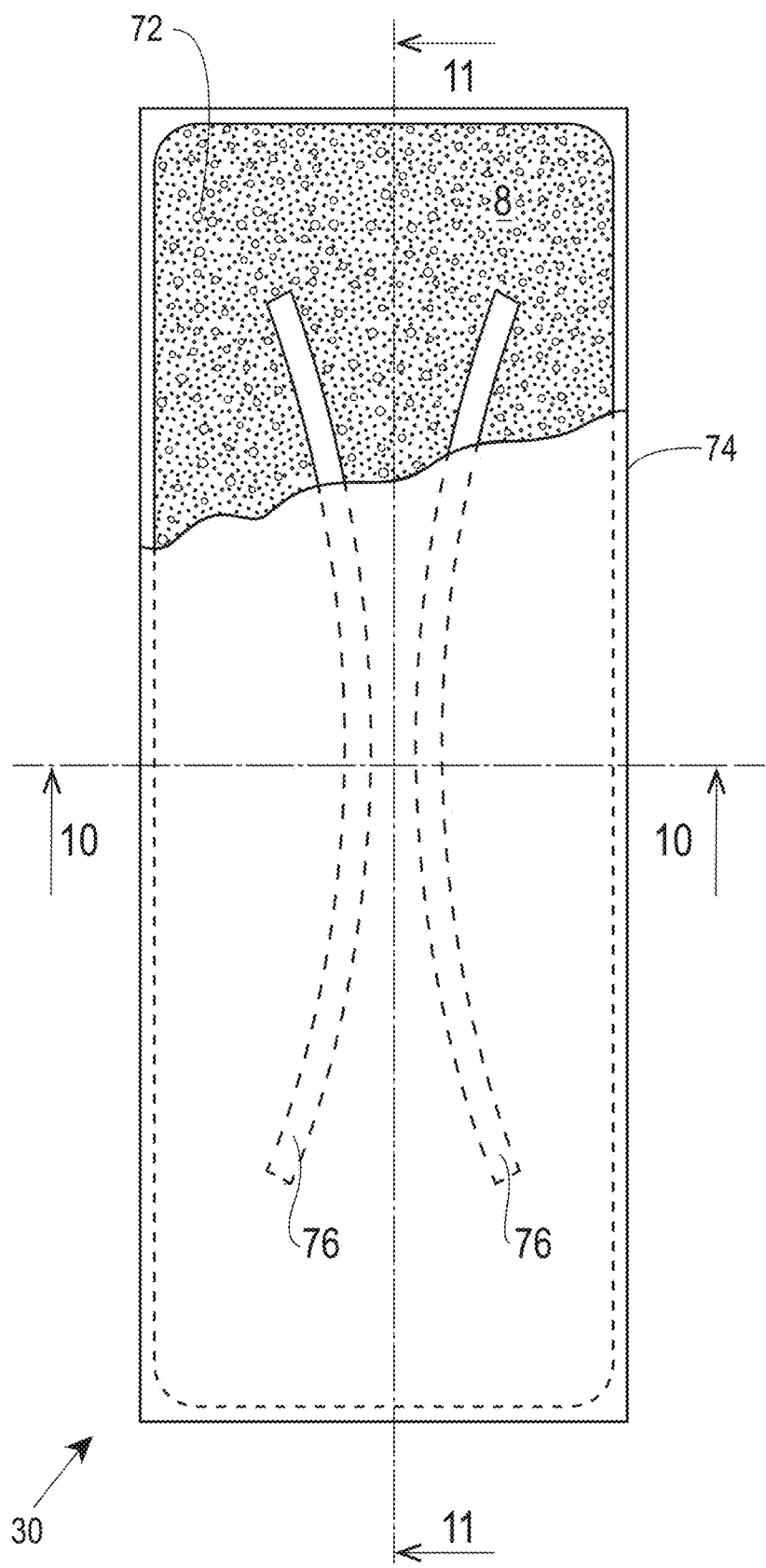
FIG. 9 is a plan view of an example absorbent core or an absorbent article.
Figures 10, 11:
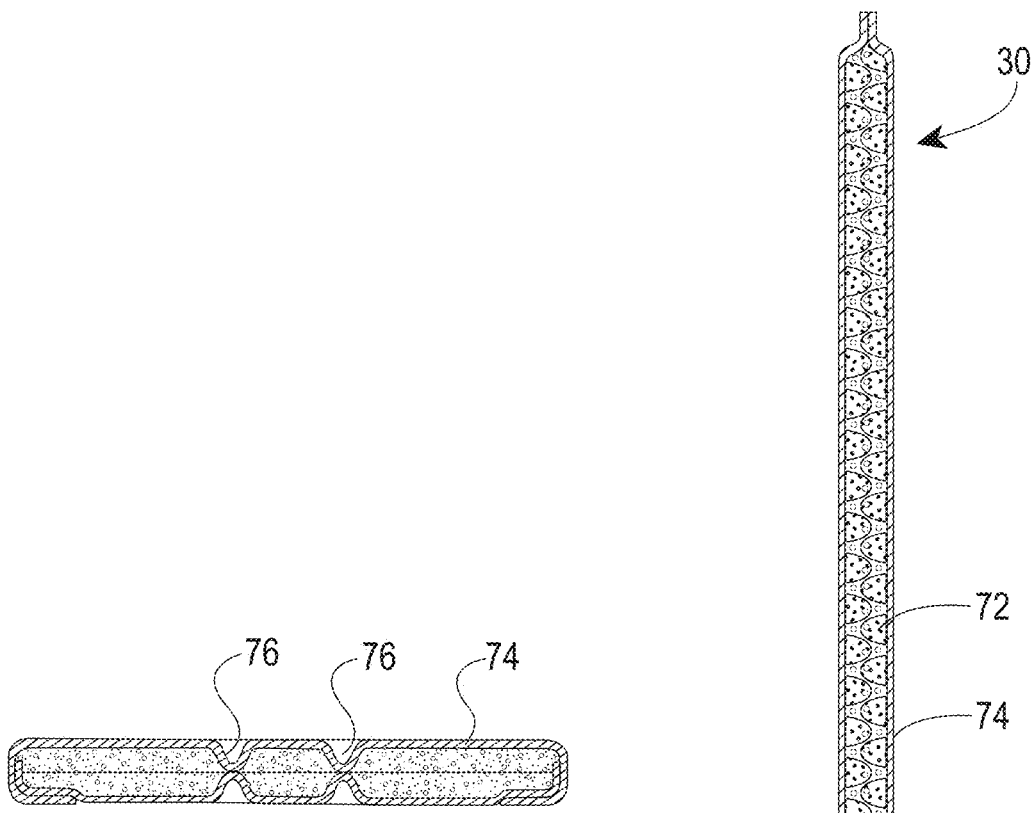
FIG. 10 is a cross-sectional view, taken about line 10-10, of the absorbent core of FIG. 9.
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material. In some instances, the acquisition material may comprise the repeating pattern of apertures comprising the plurality of repeat units discussed herein.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa. The landing zone may comprise the repeating pattern of apertures comprising the plurality of repeat units discussed herein.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof). The packages may have the same brand and/or sub-brand and/or the same trademark registration and/or having been manufactured by or for a common manufacturer and the packages may be available at a common point of sale (e.g. oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Sanitary Napkin

Figure 12:
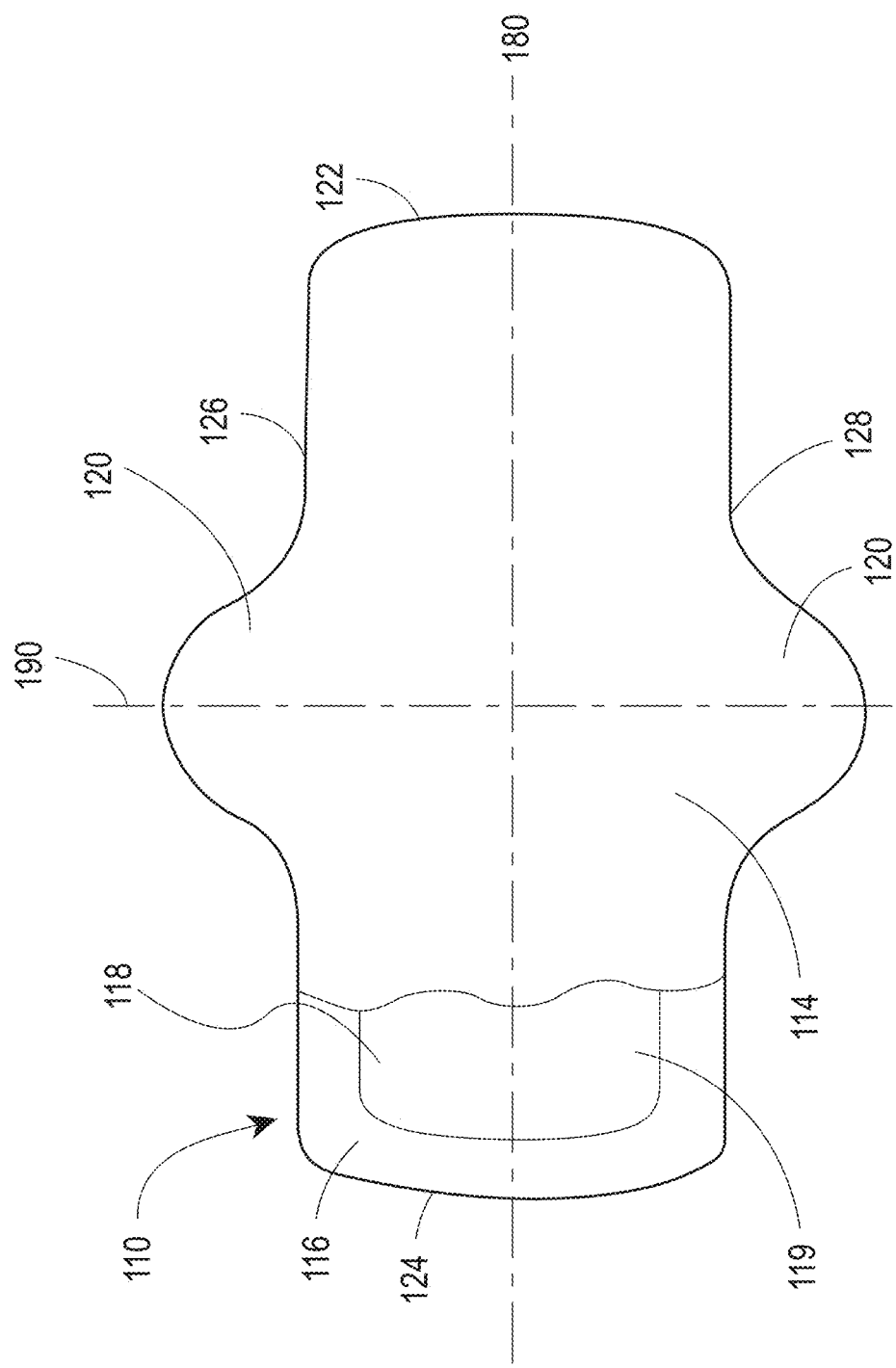
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. The topsheet or secondary topsheet of the sanitary napkin may comprise the repeating pattern of apertures comprising the plurality of repeat units discussed herein.

Examples Cross-sections of Absorbent Articles

Figure 13:
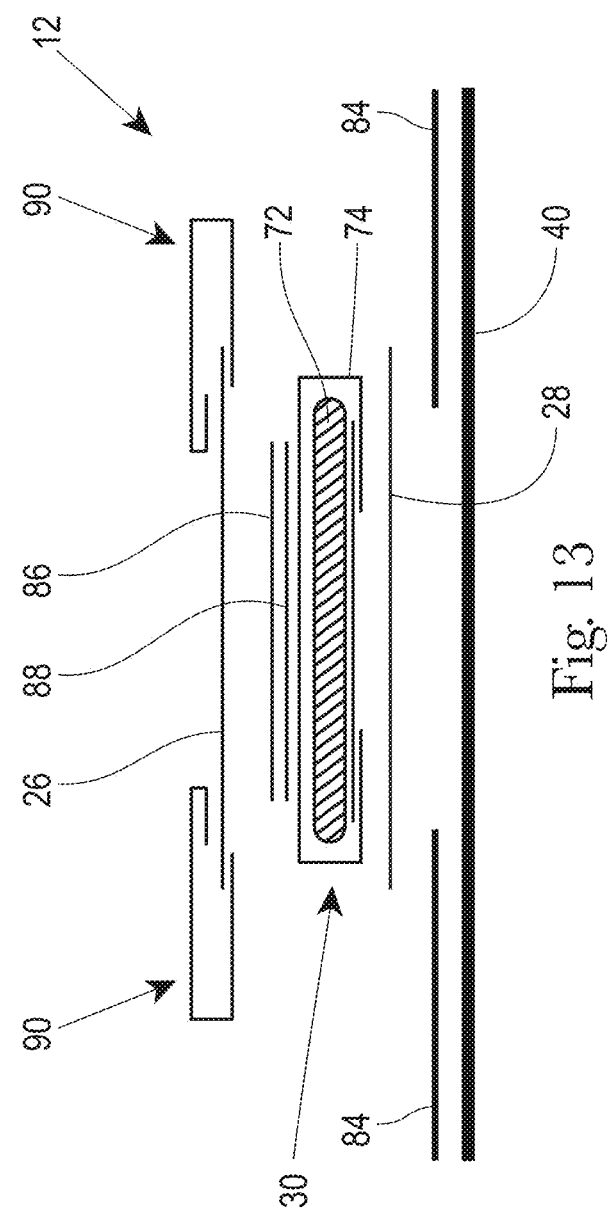
FIG. 13 is an example cross-sectional view taken within a front waist region of an absorbent article.
Figure 14:
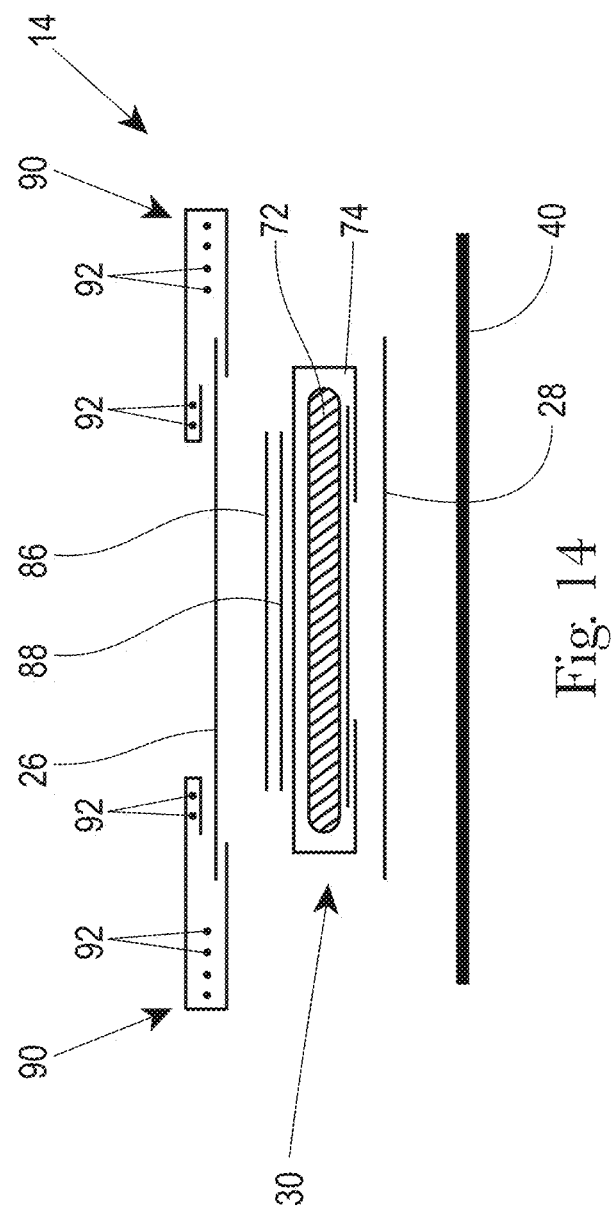
FIG. 14 is an example cross-sectional view taken within a crotch region of an absorbent article.
Figure 15:
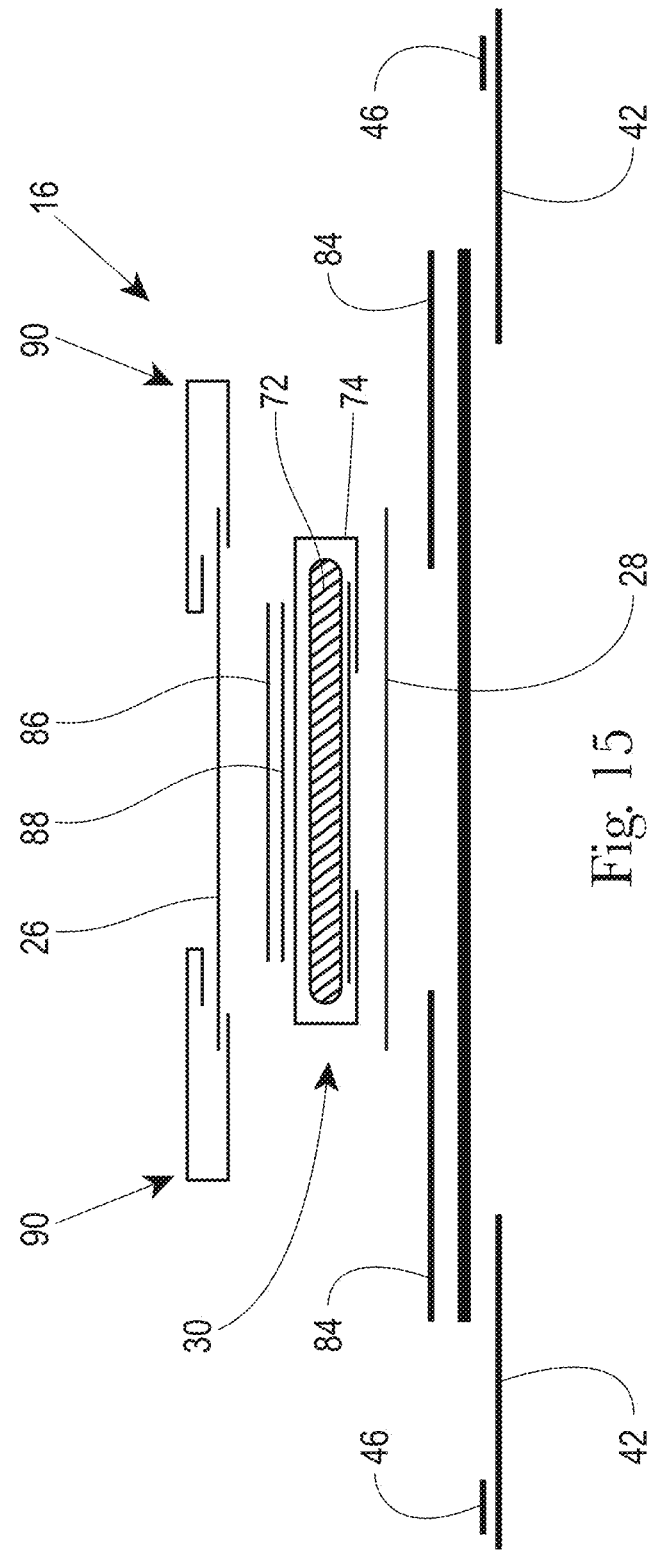
FIG. 15 is an example cross-sectional view taken within a back waist region of an absorbent article.

FIGS. 13-15 illustrate example cross-sectional views of absorbent articles within the scope of the present disclosure.

FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Substrates

The substrates in the absorbent articles having the repeating pattern of apertures comprising the plurality of repeat units may be topsheets, topsheet laminates, acquisition materials, topsheet and acquisition material laminates, outer cover nonwoven materials, nonwoven materials of ears, landing zones, and/or other substrates in absorbent articles. The substrates may have one or more layers. In various instances, the substrates or topsheets may comprise one or more nonwoven materials, one or more films, or one or more nonwovens and one or more films, for example. The repeating pattern of apertures comprising the plurality of repeat units will be discussed in the topsheet context below, but the present disclosure covers other substrates and/or laminates in an absorbent article. The repeating pattern of apertures comprising the plurality of repeat units may be used for more than one component of an absorbent article, such as a topsheet and an outer cover nonwoven material, for example. In another instance, the topsheet and the outer cover nonwoven material may have the same pattern, but the topsheet may utilize apertures to create the pattern and the outer cover nonwoven material may utilize embossing to create the same or a similar pattern.

Topsheets

The topsheets of the absorbent articles discussed above are now described in greater detail. The topsheets may each comprise one or more nonwoven materials and/or one or more films. Each nonwoven material may have one or more layers (i.e., Spunbond-meltblown-spunbond). Any of the layers may comprise cotton or natural fibers. In an example, a topsheet may have two layers of a nonwoven material. A first layer may form a wearer-facing surface of the topsheet in the absorbent article and a second layer may form a garment-facing surface of the topsheet in the absorbent article. The first and second layers may be hydrophobic or hydrophilic. The first layer may be more hydrophobic or more hydrophilic than the second layer. The first layer may be hydrophobic, while the second layer may be hydrophilic. Both layers may be hydrophobic or hydrophilic. The topsheet may comprise spunbond fibers, carded fibers, cotton fibers, meltblown fibers, nanofibers (i.e., less than one micro), and/or other suitable type of fibers (natural or synthetic). The first layer and/or the second layer may comprise spunbond fibers. The first layer may comprise spunbond fibers or carded fibers and the second layer may comprise spunbond fibers or carded fibers. The topsheet may comprise a whitening or opacifying agent, such as Titanium Dioxide, for example. The apertures of the repeating pattern of apertures may extend through all layers of a topsheet or may extend through less than all layers of a topsheet. For example, a first layer of a topsheet may have apertures while a second layer may not. The topsheets or substrates may comprise printing, ink, colored glues, and/or indicia on one or more layers thereof. Any of the layers may be tinted or colored (other than white). For example, a first layer may be white and a second layer may be light blue. As another example, the first layer may be light blue while a second layer may be dark blue. The various layers may or may not have the same color and/or opacity.

Repeat Units

The topsheets of the present disclosure may comprise a plurality of repeat units. Each of the repeat units may have at least two (or 3, or 4, or 5 etc.) apertures having a different size, shape, aspect ratio (i.e., major axis to minor axis), and/or angle relative to a central longitudinal axis of a topsheet on an absorbent article. In another instance, each of the repeat units may have at least 3 (or 4, or 5 etc.) apertures having a different size, shape, aspect ratio, and/or angle relative to the central longitudinal axis of a topsheet on an absorbent article. Each repeat unit will have at least three apertures, and likely more than three apertures. In some instances, all of the apertures in a repeat unit may be the same or different in size, shape, aspect ratio, and/or angle relative to the central longitudinal axis of a topsheet on an absorbent article. In other instances, some of the apertures in a repeat unit may be the same or different in size, shape, aspect ratio, and/or angle relative to the central longitudinal axis of a topsheet in an absorbent article. When it is said that the various apertures in a repeat until are "the same" or "different" this means the design is intended to be the same or different and is not merely process tolerances.

In an instance, substrates or topsheets comprising repeating patterns of apertures comprising the plurality of repeat units may have repeat units that all have the same apertures. Stated another way, all of the apertures in a repeat unit may be the same size, shape etc. and the repeat units may all be the same or at least a majority of the repeat units may be the same.

Figure 16:
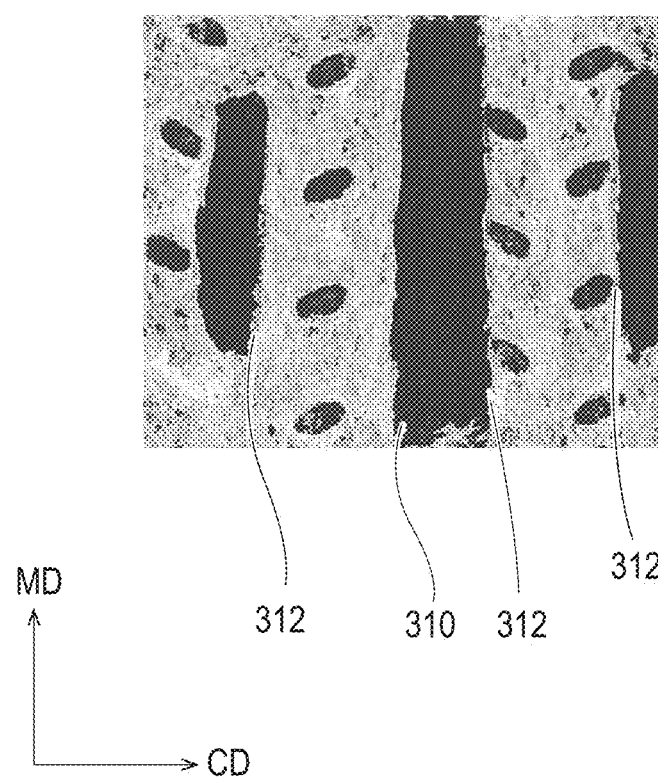
FIG. 16 is a photograph of a portion of repeat unit with apertures, wherein perimeters of at least some of the apertures comprise a melt lip.
Figure 17:
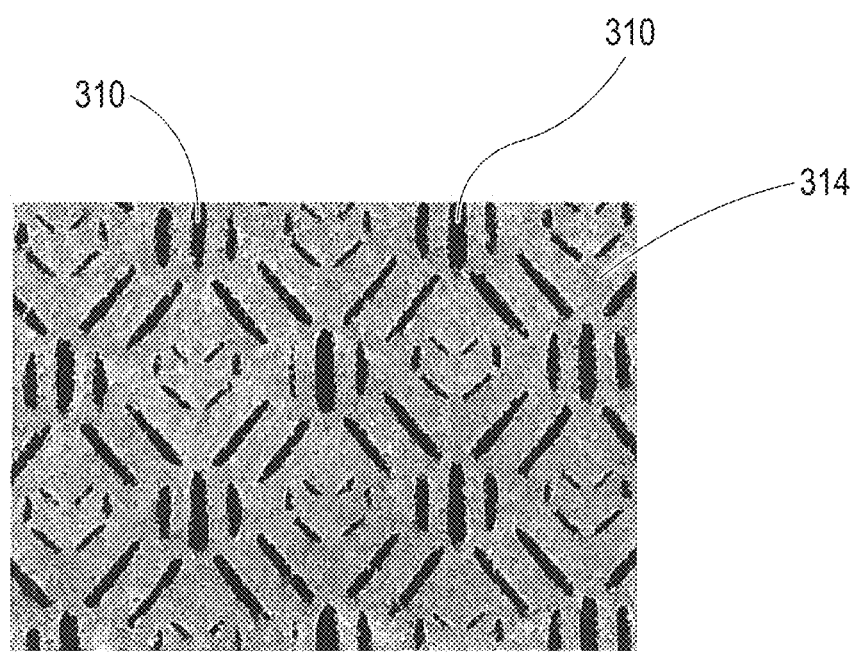
FIGS. 17 and 18 are photographs of portions of topsheets comprising repeating patterns of apertures comprising a plurality of repeat units.
Figure 18:
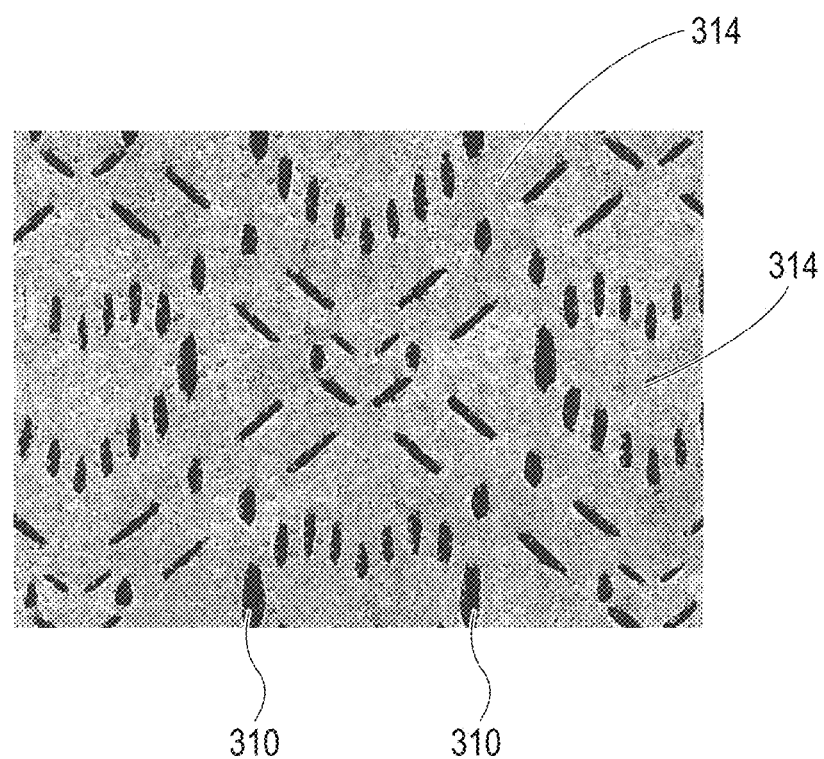
Figure 19:
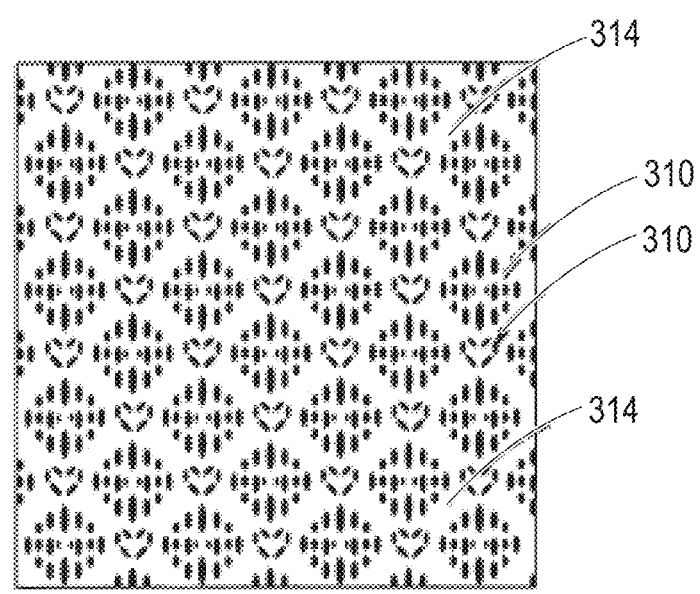
FIGS. 19-21 are schematic illustrations of portion of topsheets comprising repeating patterns of apertures comprising a plurality of repeat units.

In some examples, and referring to FIG. 16, portions of perimeters of at least some of the apertures 310 in the repeat units may comprise one or more melt lips 312 or fused portions. In some examples, portions of perimeters of at least some of the apertures may be free of a melt lip. Thus, in certain examples, the one or more melt lips 312 may at least partially or fully surround the apertures 310. In an example, the one or more melt lips 312 may surround from about 25% of a perimeter of the apertures 310 to about 100% of the perimeter of the apertures 310. In certain examples, the one or more melt lips 312 may be formed on lateral sides of the apertures 310 and not on leading and/or trailing edges of the apertures 310 (see MD and CD arrows for reference in FIG. 16). It is believed that the one or more melt lips 312 may be formed during an overbonding step (as taught in U.S. Pat. Appl. Publication No. 2016/0136014 to Arora et al.) and may add strength to an apertured topsheet, for example.

Examples of portions of substrates or topsheet comprising repeating patterns of apertures comprising a plurality of repeat units are illustrated in FIGS. 17-21. Apertures are identified as 310 and land areas are identified as 314. Additional aperture patterns and configurations, including example methods of making are disclosed in U.S. Pat. Appl. Pub. No. 2016/0136014 to Arora et al.

Various suitable processes for aperturing the substrates or topsheets described herein may be utilized. For example, the apertures in the substrates or topsheets may be formed by hydroforming carded webs, laser cutting, punching with a patterned roll, hot pin methods, overbonding and ring rolling as disclosed in U.S. Pat. Appl. Publication No. US 2016/0136014, or other suitable methods. Additional aperturing processes that may be utilized are described in U.S. Pat. Nos. 9,023,261, 8,158,043, 8,241,543, and 8,679,391, for example.

Figure 20:
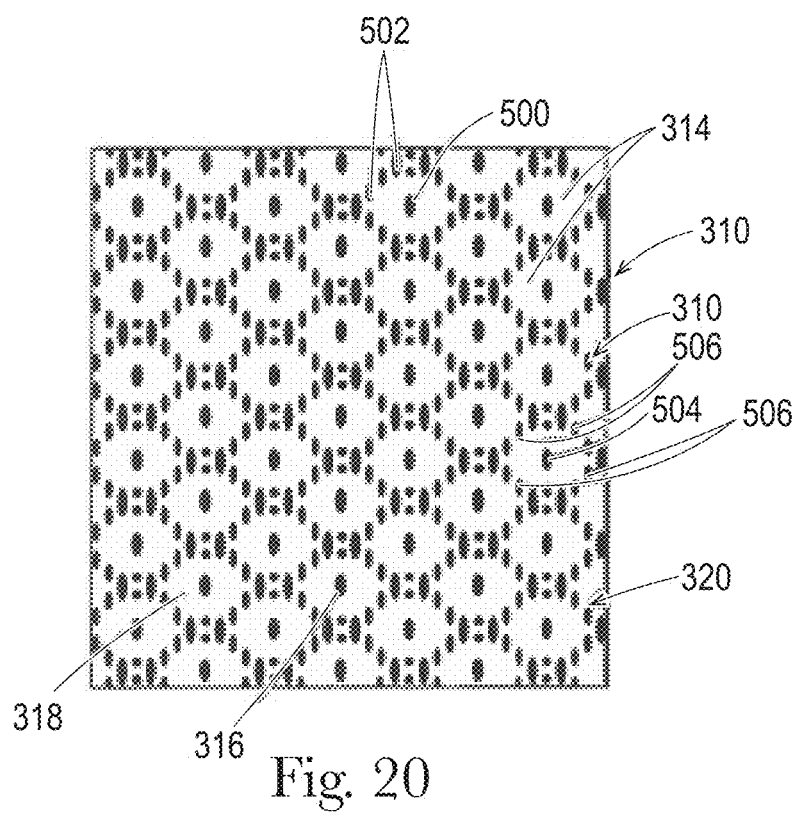
Figure 21:
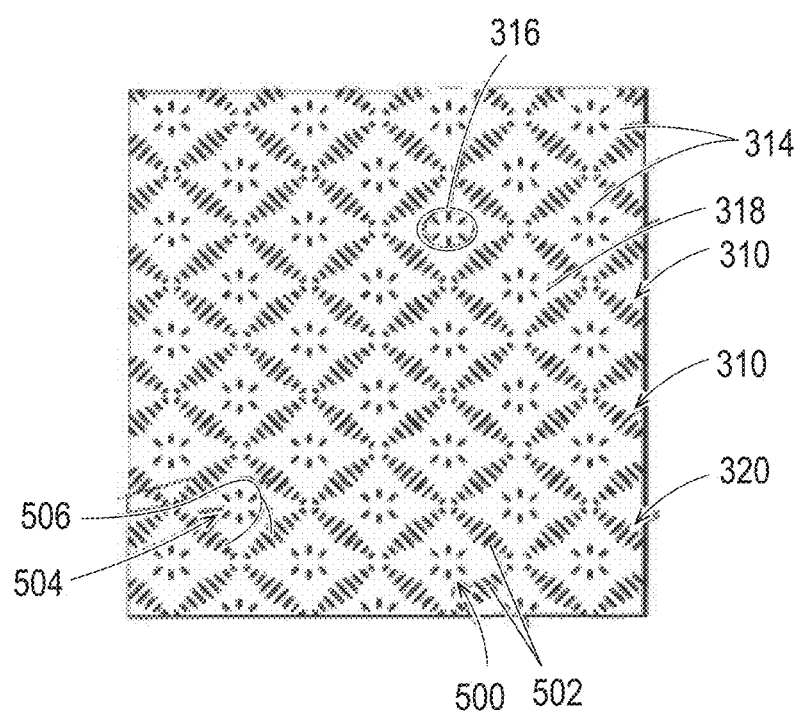

Referring to FIGS. 20 and 21, an equity element 316 may be present in a central area of each repeat unit, or less than each repeat unit. The equity element 316 may be a heart, leaf, star, logo, brand identifier, or any other suitable element. The equity element 316 may have a defined space 318 surrounding it in at least a majority of the repeat units. The defined space 318 may be a land area without apertures. In certain patterned repeat units, it may be important to have this defined space 318 surrounding the equity element 316 to allow the equity element 316 to stand out to a viewer. The defined space 318 may be surrounded by a grid of apertures 320. The grid of apertures 320 may have apertures that are different or the same in size, shape, aspect ratio, and/or angle relative to the central longitudinal axis of a topsheet on an absorbent article compared to the aperture or apertures forming the equity element. The grid may form a diamond pattern. The grid may be formed of one or more rows of apertures.

Referring again to FIGS. 20 and 21, at least some of the apertures in one or more of the repeat units may be different in size and/or shape than other apertures in the one or more repeat units, excluding process tolerances. Further, at least some of the apertures in one or more repeat units may be the same in size and/or shape as other apertures in the one or more repeat units, excluding process tolerances. Each repeat unit, or some repeat units, may comprise a central region of one or more apertures 500 that is spaced apart from other apertures 502. Each repeat unit, or some repeat units, may comprise a central pattern of one or more apertures 504 that may be fully, or partially surrounded by an outer pattern of apertures 506.

Substantially Similar Repeat Units

Figure 22:
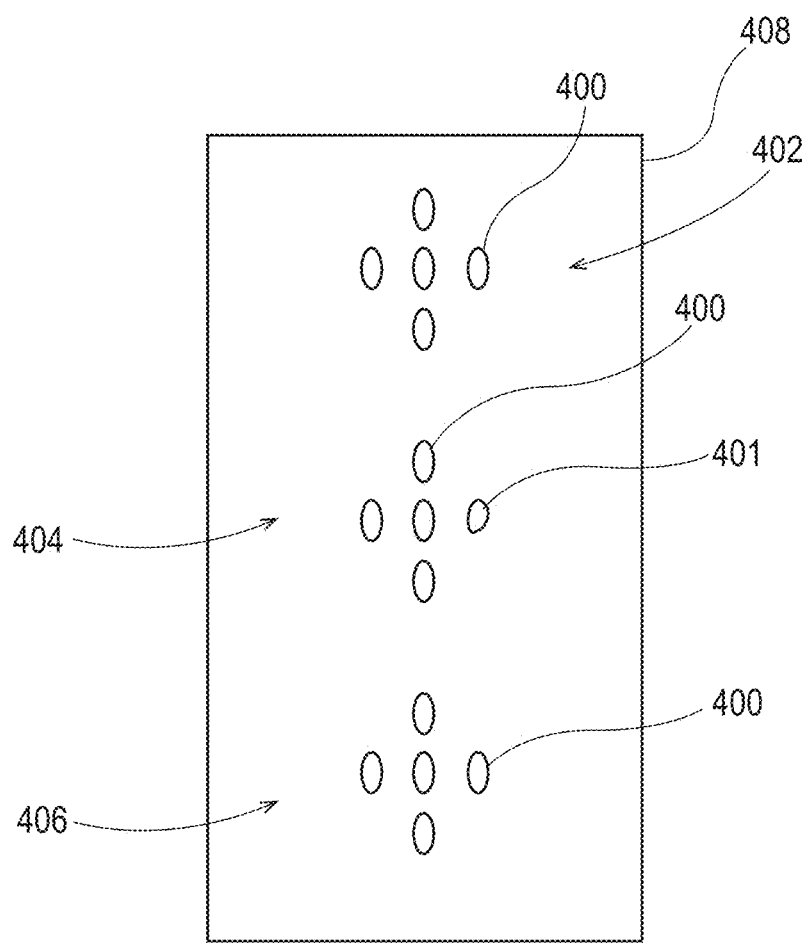
Figure 23:
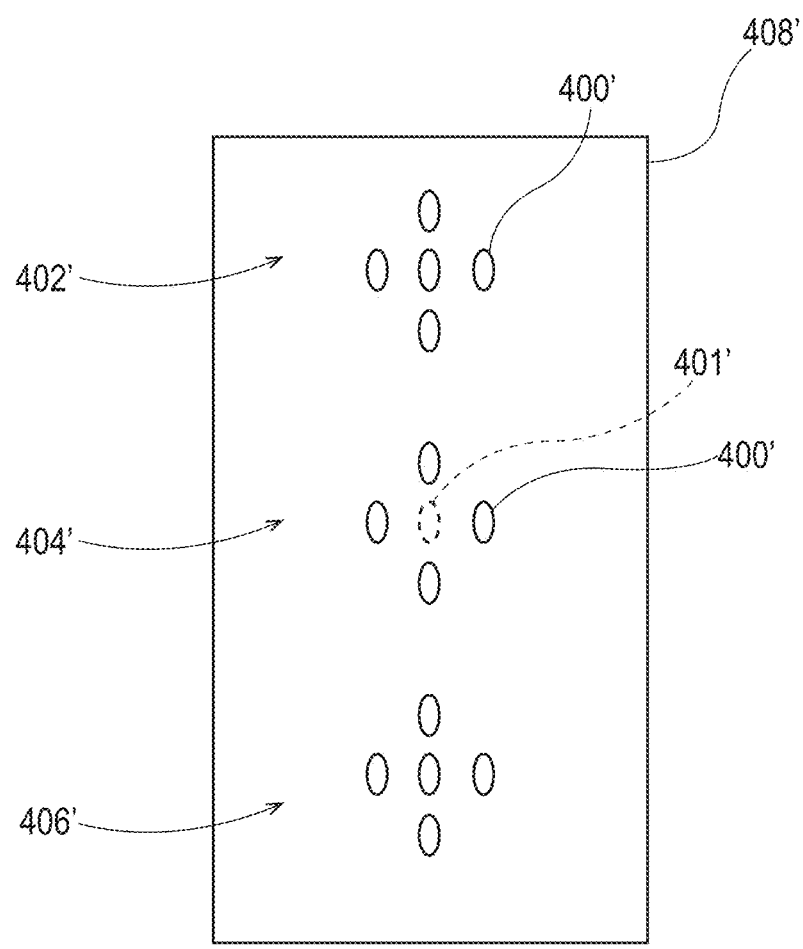

Although, in some instances, the apertures in each repeat unit are generally designed to be the same, process variations may cause the repeat units to appear slightly different. Examples of repeat units that are substantially similar are illustrated in FIGS. 22 and 23. Referring to FIG. 22, a repeating pattern of apertures 400 comprising a plurality of repeat units 402, 404, and 406 are illustrated in a substrate 408. The apertures 400 in the repeat units 402 and 406 are the same, but at least one aperture 401 in the repeat unit 404 is slightly different from the apertures 400. This could be from process conditions were the aperture 401 did not fully form or rupture or from variations in a precursor material. Referring to FIG. 23, a repeating pattern of apertures 400' comprising a plurality of repeat units 402', 404', and 406' are illustrated in a substrate 408'. The apertures in the repeat units 402' and 406 are the same, but at least one aperture 401' is slightly different from the apertures 400'. This could be from process conditions were the aperture 401' did not form or rupture or from variations in a precursor material. The repeat units 402, 404, and 406 may be considered substantially the same and, likewise, the repeat units 402', 404', and 406' may be considered substantially the same. In other instances, various apertures of the repeat unit may be slightly angled relative to a central longitudinal axis or a central lateral axis and the repeat units may still be considered substantially the same. Also, the shapes and sizes of the various apertures in the various repeat units may be slightly different and the repeat units may still be considered substantially the same.

Aperture Aspect Ratio

The apertures of the repeating pattern of apertures comprising the plurality of repeat units may have an aspect ratio of greater than one, for example, greater than two, greater than 3, greater than 5, or greater than 10, but typically less than 15, according to the Aperture Test herein. The repeat units may comprise apertures having more than one aspect ratio, such as two or more distinct populations or having a substantially continuous distribution of aspect ratios having a slope greater than zero. Additionally, the repeat units may comprise apertures with more than two effective aperture areas, either as two or more distinct populations or as a distribution of aperture areas having a slope greater than zero. The Relative Standard Deviation of the aperture aspect ratios in the apertures of the repeating pattern of apertures comprising repeat units may be at least about 30%, at least about 40%, or at least about 45%.

Aperture Density

The apertures of the repeating pattern of apertures comprising the plurality of repeat units may have an Aperture Density, according to the Aperture Test herein, of at least about 150, at least about 175, at least about 200, or at least about 300, but less than 1,000, for example.

% Effective Open Area

The topsheets or substrates comprising the repeating pattern of apertures comprising the plurality of repeat units may have an Effective Open Area between about 3% to about 50%, about 5% to about 50%, about 5% to about 40%, about 5% to about 30%, about 5% to about 25%, about 5% to about 20%, or about 5% to about 15%, specifically reciting all 0.1% increments within the specified ranges and all ranges formed therein or thereby. All Effective Open Area percentages are determined using the Aperture Test described herein.

Effective Aperture Area

The topsheets or substrates comprising the repeating pattern of apertures comprising the plurality of repeat units may have apertures having an Effective Aperture Area in the range of about 0.3 $mm^2$ to about 15 $mm^2$, 0.3 $mm^2$ to about 14 $mm^2$, 0.4 $mm^2$ to about 12 $mm^2$, 0.3 $mm^2$ to about 10 $mm^2$, 0.5 $mm^2$ to about 8 $mm^2$, or 1.0 $mm^2$ to about 8 $mm^2$, specifically reciting all 0.05 $mm^2$ increments within the specified ranges and all ranges formed therein or thereby. All Effective Aperture Areas are determined using the Aperture Test described herein. A plurality of the apertures in the repeating pattern of apertures comprising the plurality of repeat units may be different in Effective Aperture Areas. The Relative Standard Deviation of the Effective Aperture Areas in the repeating pattern of apertures comprising the plurality of repeat units may be at least about 50%, or at least about 55%, or at least about 60%, for example.

Repeat Unit Measurements

The various repeat units may have certain characteristics, such as repeat unit area (overall X-Y plane area of the repeat unit), repeat unit width, repeat unit length, for example. Absorbent articles comprising topsheets or substrates comprising a repeating pattern of apertures having a plurality of repeat units may have certain numbers of repeat units relative to the absorbent article's dimensions and/or total area. Those properties are discussed below.

Repeat Unit Area

All of or a majority of individual repeat units in a repeating pattern of apertures comprising a plurality of repeat units of a topsheet or substrate may have a repeat unit area in the range of about 200 mm$^2$ to about 2,000 mm$^2$, about 500 mm$^2$ to about 1,750 mm$^2$, about 900 mm$^2$ to about 1500 mm$^2$, about 730 mm$^2$ to about 1,500 mm$^2$, about 730 mm$^2$ to about 1,300 mm$^2$, about 700 mm$^2$ to about 1,500 mm$^2$, about 750 mm$^2$ to about 1,500 mm$^2$, about 1,000 mm$^2$ to about 1,500 mm$^2$, about 1,100 mm$^2$ to about 1,400 mm$^2$, about 1,150 mm$^2$ to about 1,300 mm$^2$, about 500 mm$^2$ to about 1,300 mm$^2$, about 600 mm$^2$ to about 1,100 mm$^2$, about 650 mm$^2$ to about 1,100 mm$^2$, about 700 mm$^2$ to about 1,110 mm$^2$, about 700 mm$^2$ to about 1,000 mm$^2$, about 750 mm$^2$ to about 1000 mm$^2$, about 725 mm$^2$ to about 975 mm$^2$, about 730 mm$^2$ to about 750 mm$^2$, about 785 mm$^2$ to about 805 mm$^2$, about 860 mm$^2$ to about 880 mm$^2$, about 940 mm$^2$ to about 960 mm$^2$, about 200 mm$^2$ to about 600 mm$^2$, or about 250 mm$^2$ to about 600 mm$^2$, specifically reciting all 0.1 mm$^2$ increments within the specified ranges and all ranges formed therein or thereby. The repeat unit area may also be about 951 mm$^2$. Repeat unit areas are measured according to the Repeat Unit Measurement Test herein.

Repeat Unit Width

All of or a majority of individual repeat units in a repeating pattern of apertures comprising a plurality of repeat units of a topsheet or substrate may have a repeat unit width in the range of about 10 mm to about 100 mm, about 25 mm to about 75 mm, about 30 mm to about 70 mm, about 35 mm to about 65 mm, about 45 mm to about 55 mm, about 35 mm to about 55 mm, about 40 mm to about 60 mm, about 45 mm to about 55 mm, about 50 mm, about 10 mm to about 50 mm, about 15 mm to about 50 mm, about 20 mm to about 50 mm, about 25 mm to about 50 mm, about 30 mm to about 45 mm, about 34 mm to about 42 mm, or about 35 mm to about 41 mm, about 34 mm to about 36 mm, about 36 mm to about 38 mm, about 40 mm to about 42 mm, specifically reciting all 0.1 mm increments within the specified ranges and all ranges formed therein or thereby. The repeat unit width may also be about 41 mm. Repeat unit widths are measured according to the Repeat Unit Measurement Test herein.

Repeat Unit Length

All of or a majority of individual repeats unit in a repeating pattern of apertures comprising a plurality of repeat units of a topsheet or substrate may have a repeat unit length in the range of about 10 mm to about 100 mm, about 25 mm to about 75 mm, about 35 mm to about 65 mm, about 35 mm to about 55 mm, about 35 to about 50, about 40 mm to about 60 mm, about 45 mm to about 55 mm, about 50 mm, about 51 mm, about 51.5 mm, about 15 mm to about 50 mm, about 20 mm to about 50 mm, about 25 mm to about 50 mm, about 30 mm to about 45 mm, about 34 mm to about 38 mm, about 35 mm to about 37 mm, about 40 mm to about 44 mm, about 41 mm to about 43 mm, specifically reciting all 0.1 mm increments within the specified ranges and all ranges formed therein or thereby. The repeat unit length may also be about 42 mm. Repeat unit lengths are measured according to the Repeat Unit Measurement Test herein.

Repeat Units Per Total Length of an Absorbent Article

An absorbent article may have a certain number of repeat units per the total length of the absorbent article in the range of about 3 to about 30, about 3 to about 25, about 4 to about 18, about 5 to about 16, about 5 to about 12, about 6 to about 16, about 6.1 to about 15.8, about 4 to about 20, about 5 to about 20, about 5 to about 18, about 6 to about 17, about 7 to about 16, about 7.5 to about 15.8, or about 7.5 to about 13.4, specifically reciting all 0.1 increments within the specified ranges and all ranges formed therein or thereby. Repeat units per total length of an absorbent article are measured according to the Repeat Unit Measurement Test herein.

Repeat Units Per Total Width of an Absorbent Article

An absorbent article may have a certain number of repeat units per total width of the absorbent article in the range of about 2 to about 10, about 2 to about 8, about 2 to about 7.5, about 2.5 to about 7, about 3 to about 7, about 3 to about 5, about 3 to about 6.5, about 3.2 to about 6.3, about 3.5 to about 6.5, about 4 to about 6.5, about 4 to about 6.3, or about 4 to about 5.4, specifically reciting all 0.1 increments within the specified ranges and all ranges formed therein or thereby. Repeat units per total width of an absorbent article are measured according to the Repeat Unit Measurement Test herein.

Repeat Units Per Total Area of an Absorbent Article

An absorbent article may have a certain number of repeat units per total area of an absorbent article in the range of about 20 to about 220, about 30 to about 220, about 30 to about 210, about 30 to about 200, about 35 to about 110, about 35 to about 200, about 30 to about 180, about 35 to about 180, about 35 to about 175, about 40 to about 170, about 41.7 to about 170, about 40 to about 190, about 45 to about 185, about 50 to about 175, about 53 to about 170, about 53.6 to about 169.7, or about 53.6 to about 132.3, specifically reciting all 0.1 increments within the specified ranges and all ranges formed therein or thereby. The repeat units per total area of an absorbent article are measured according to the Repeat Unit Measurement Test herein.

TABLE 1

| | S0 | S1 | S2 | S3 | S4 | S5 | S6 | S7 |
|---|---|---|---|---|---|---|---|---|
| Absorbent Article Dimensions | | | | | | | | |
| Length (mm) | 315 | 373 | 403 | 440 | 488 | 516 | 528 | 567 |
| Width (mm) | 162 | 206 | 206 | 206 | 206 | 222 | 222 | 222 |
| Area (mm$^2$) | 51,030 | 76,838 | 83,018 | 90,640 | 100,528 | 114,552 | 117,216 | 125,874 |

| | Width (mm) | Length (mm) | Area (mm$^2$) |
|---|---|---|---|
| Repeat Unit Dimensions | | | |
| Pattern 1 | 35.2 | 36.4 | 792.8 |
| Pattern 2 | 37.3 | 35.9 | 868.1 |
| Pattern 3 | 40.9 | 42.2 | 951.2 |
| Pattern 4 | 35.0 | 36.1 | 741.7 |
| Pattern 5 | 50.0 | 51.5 | 1,225.0 |

| | S0 | S1 | S2 | S3 | S4 | S5 | S6 | S7 |
|---|---|---|---|---|---|---|---|---|
| Repeat Units/Total Absorbent Article Length | | | | | | | | |
| Pattern 1 | 8.7 | 10.2 | 11.1 | 12.1 | 13.4 | 14.2 | 14.5 | 15.6 |
| Pattern 2 | 8.8 | 10.4 | 11.2 | 12.3 | 13.6 | 14.4 | 14.7 | 15.8 |
| Pattern 3 | 7.5 | 8.8 | 9.5 | 10.4 | 11.6 | 12.2 | 12.5 | 13.4 |
| Pattern 4 | 8.7 | 10.3 | 11.2 | 12.2 | 13.5 | 14.3 | 14.6 | 15.7 |
| Pattern 5 | 6.1 | 7.2 | 7.8 | 8.5 | 9.5 | 10.0 | 10.3 | 11.0 |
| Repeat Units/Total Absorbent Article Width | | | | | | | | |
| Pattern 1 | 4.6 | 5.9 | 5.9 | 5.9 | 5.9 | 6.3 | 6.3 | 6.3 |
| Pattern 2 | 4.3 | 5.5 | 5.5 | 5.5 | 5.5 | 6.0 | 6.0 | 6.0 |
| Pattern 3 | 4.0 | 5.0 | 5.0 | 5.0 | 5.0 | 5.4 | 5.4 | 5.4 |
| Pattern 4 | 4.6 | 5.9 | 5.9 | 5.9 | 5.9 | 6.3 | 6.3 | 6.3 |
| Pattern 5 | 3.2 | 4.1 | 4.1 | 4.1 | 4.1 | 4.4 | 4.4 | 4.4 |
| Repeat Units/Total Absorbent Article Area | | | | | | | | |
| Pattern 1 | 64.4 | 96.9 | 104.7 | 114.3 | 126.8 | 144.5 | 147.9 | 158.8 |
| Pattern 2 | 58.8 | 88.5 | 95.6 | 104.4 | 115.8 | 132.0 | 135.0 | 145.0 |
| Pattern 3 | 53.6 | 80.8 | 87.3 | 95.3 | 105.7 | 120.4 | 123.2 | 132.3 |
| Pattern 4 | 68.8 | 103.6 | 111.9 | 122.2 | 135.5 | 154.4 | 158.0 | 169.7 |
| Pattern 5 | 41.7 | 62.7 | 67.8 | 74.0 | 82.1 | 93.5 | 95.7 | 102.8 |

The above discussed repeat unit measurements were tested for various absorbent article sizes and for sample repeating patterns of apertures comprising a plurality of repeat units as the topsheet of the absorbent articles as illustrated below. All testing was in accordance with the Repeat Unit Measurement Test herein. "S" in Table 1 below means size of an absorbent article as they are made commercially, although the present disclosure also includes adult incontinence sizes and preemie sizes of absorbent articles.

Embossing

As an alternative execution, a substrate or a topsheet may comprise a repeating pattern of embossments comprising a plurality of repeat units formed by embossing instead of using apertures. The embossments/repeat units formed by embossing may have the same measurements as expressed above with respect to the repeating patterns of apertures comprising the plurality of repeat units and may be measured using the Repeat Unit Measurement Test. As a further execution, a top sheet or a substrate may comprise a repeating pattern comprising the plurality of repeat units formed of embossments and apertures, while still retaining the same measurements expressed above with respect to the repeating patterns of apertures comprising the plurality of repeat units.

Zones of Repeat Units

In some instances, zones of repeat units may be present in topsheets or substrates of absorbent articles. The zones may be suitably positioned for urine, BM, or menses acquisition. The repeat units in the various zones may all be the same or may be different between the various zones.

As an example, an absorbent article may have a central lateral axis. A first repeating pattern of apertures comprising a first plurality of the same first repeat units may be on a first side of the central lateral axis. A second, different repeating pattern of apertures comprising a second plurality of the same second repeat units may be on a second side of the central lateral axis. The first and second repeat units may be different in aperture size, aperture shape, aperture aspect ratio, repeat unit area, aperture pattern, repeat unit width, and/or repeat unit length. In an instance, the pattern of the first repeat units on the first side of the central lateral axis may be the same as a second pattern of the second repeat units on the second side of the central lateral axis. In such an instance, the patterns may have the same aesthetic appearance, but may be different scales (e.g., repeat unit areas on one side of the lateral axis are smaller). In other instances, the aesthetic appearance of the first repeat units may be different than the second repeat units.

A similar concept may apply to zones that are on a first side of central longitudinal axis and a second side of the central longitudinal axis. Alternatively, a first zone may be surrounded by a second zone. In some instances, more than two, or more than three zones may be provided. Any of the various zones may have any suitable size and shape.

Materials

Some topsheets or substrates of the present disclosure may comprise PE/PP bicomponent fiber spunbond webs.

Other suitable webs may comprise spunbond webs comprising side-by-side crimped fibers (e.g., PE/PP or PP/PP) that are bonded via calendar (thermal point) bonding or through-air bonding. Other suitable webs may comprise carded, through-air bonded or resin bonded (highloft) nonwovens comprising PE/PP or PE/PET fibers. The webs may comprise nanofibers, optionally with other fibers. In some instances, multiple layer webs may be desired over a single layer webs (even at the same basis weight) due to increased uniformity/opacity and the ability to combine webs having different properties. For example, an extensible spunbond nonwoven carrier layer may be combined with a soft, highloft nonwoven (spunbond or carded) to create an apertured web that is both soft and strong. The layers may have the same or different surface energy. For example, a top layer of a topsheet or substrate may be hydrophobic and the lower layer may be hydrophilic. The layers may have different permeability/capillarity, e.g. the upper layer may have higher permeability and the lower layer have higher capillarity in order to set up a capillary gradient and aid in moving fluid away from the surface (or topsheet) of an absorbent article and into an absorbent core of the absorbent article.

Fibers of the topsheet and substrate webs may comprise any suitable thermoplastic polymers. Example thermoplastic polymers are polymers that melt and then, upon cooling, crystallize or harden, but that may be re-melted upon further heating.

The thermoplastic polymers may be derived from any suitable material including renewable resources (including bio-based and recycled materials), fossil minerals and oils, and/or biodegradable materials. Some suitable examples of thermoplastic polymers include polyolefins, polyesters, polyamides, copolymers thereof, and combinations thereof. Polypropylene and/or polypropylene copolymers, including atactic polypropylene; isotactic polypropylene, syndiotactic polypropylene, and combination thereof may also be used.

The thermoplastic polymer component may be a single polymer species or a blend of two or more thermoplastic polymers e.g., two different polypropylene resins. As an example, fibers of a first nonwoven layer of a topsheet or substrate web may comprise polymers such as polypropylene and blends of polypropylene and polyethylene, while a second nonwoven layer of the topsheet or substrate web may comprise fibers selected from polypropylene, polypropylene/polyethylene blends, and polyethylene/polyethylene terephthalate blends. In some forms, a second nonwoven layer may comprise fibers selected from cellulose rayon, cotton, other hydrophilic fiber materials, or combinations thereof. The fibers may also comprise a super absorbent material such as polyacrylate or any combination of suitable materials.

The fibers of the topsheet or substrate webs may comprise monocomponent fibers, bi-component fibers, and/or bi-constituent fibers, round fibers or non-round fibers (e.g., capillary channel fibers), and may have major cross-sectional dimensions (e.g., diameter for round fibers) ranging from about 0.1 microns to about 500 microns. The fibers may also be a mixture of different fiber types, differing in such features as chemistry (e.g. polyethylene and polypropylene), components (mono- and bi-), denier (micro denier and >2 denier), shape (i.e. capillary and round) and the like. The fibers may range from about 0.1 denier to about 100 denier.

As used herein, the term "monocomponent fiber(s)" refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fiber(s)" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which may be used in the first nonwoven layer include polyethylene/polypropylene side-by-side bi-component fibers. Another example is a polypropylene/polyethylene bi-component fiber where the polyethylene is configured as a sheath and the polypropylene is configured as a core within the sheath. Still another example is a polypropylene/polypropylene bi-component fiber where two different propylene polymers are configured in a side-by-side configuration. Additionally, forms are contemplated where the fibers of a nonwoven layer are crimped.

Bi-component fibers may comprise two different resins, e.g. a first polypropylene resin and a second polypropylene resin. The resins may have different melt flow rates, molecular weights, or molecular weight distributions.

As used herein, the term "bi-constituent fiber(s)" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise multiconstituent components.

As used herein, the term "non-round fiber(s)" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

Other example nonwoven materials for the topsheet or substrate webs may comprise spunbond materials, carded materials, melt blown materials, spunlace materials, needle punched materials, wet-laid materials, or air-laid materials, for example.

Repeat Unit Measurement Test

An absorbent article specimen is taped to a rigid flat surface in a planar configuration with a topsheet having a repeating pattern of apertures comprising a plurality of single repeat units facing upward. The article is taped in such way as to avoid introducing distortions of the repeating pattern of apertures due to the extent of longitudinal and lateral extension of the absorbent article. Any absorbent article(s) being tested are conditioned at 23° C.±2° C. and 50%±2% relative humidity for 2 hours prior to testing. For the purposes of this method, all patterns and distances are taken to be based on the projection of the aperture pattern onto a two-dimensional plane.

A single repeat unit (hereafter "SRU") (for subsequent dimensional measurement) within the topsheet having the repeating pattern of apertures comprising the plurality of repeating units is defined as follows. An arbitrary aperture is identified, referred to hereafter as the "chosen aperture" (hereafter "CA"). Any other aperture in the topsheet recognized to be in an equivalent position based on the translational symmetry of the repeat units is referred to as an "equivalent aperture" (hereafter "EA"). The SRU is defined as the set of points that are closer (via Euclidean distance) to the center of the CA than to the center of any other EA in the topsheet. The SRU identified for measurement must not touch the edge of the topsheet. After finding all points within the SRU, if it is found that the SRU touches the edge of the topsheet, this procedure is repeated with an alternative CA. The process is repeated until a SRU that does not touch the edge of the topsheet is identified.

Figure 24:
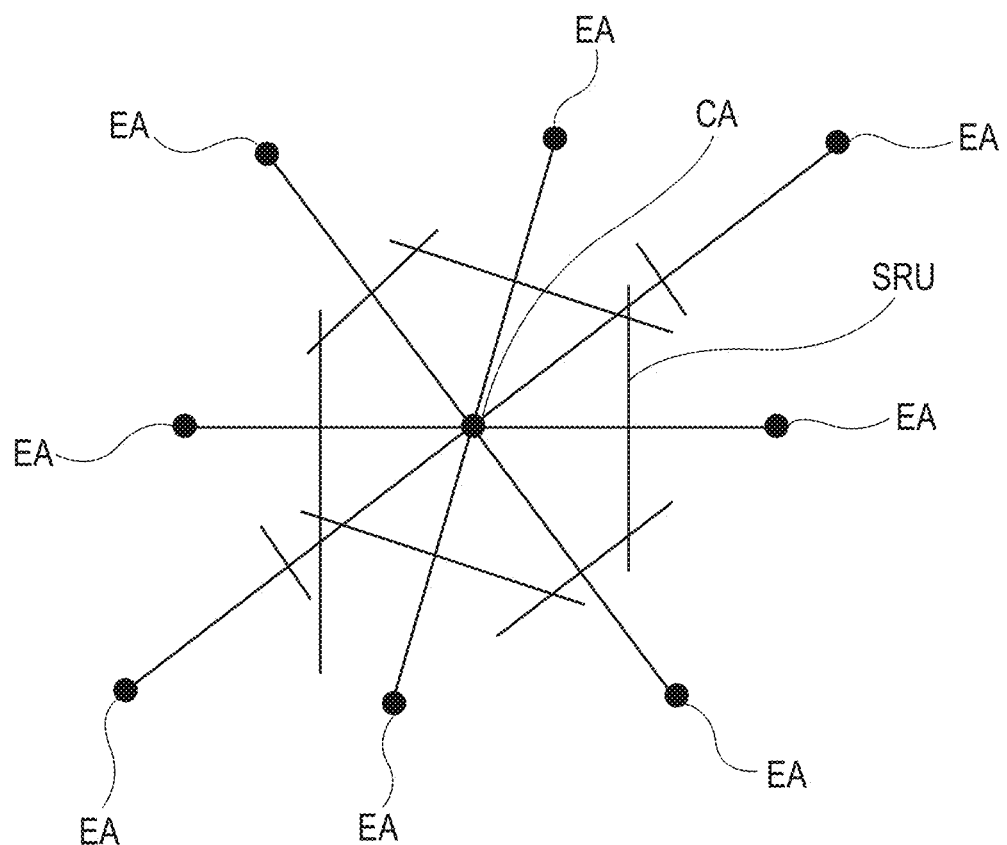
FIG. 24 is an example repeat unit boundary identification linked to the Repeat Unit Measurement Test herein.

One approach to determining the set of points of a SRU is based on identifying a polygonal boundary. Referring to FIG. 24, the boundary of the SRU is the convex polygon formed by the intersection of line segments that immediately border the topsheet region containing the CA. The line segments are identified from lines drawn perpendicular to the midpoint of lines connecting the center of the CA to the center of all neighboring and nearby EA.

Figure 25:
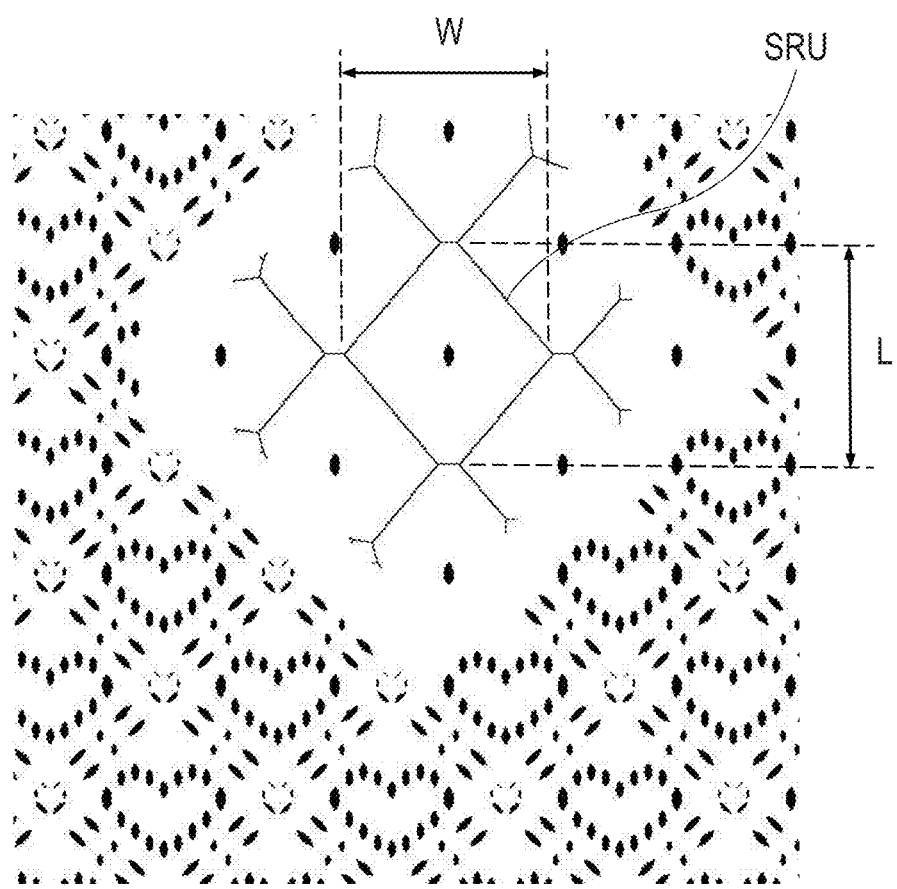
FIG. 25 is an example repeat unit boundary identification taken in a substrate comprising a repeating pattern of apertures comprising a plurality of repeat units linked to the Repeat Unit Measurement Test herein.

Referring to FIG. 25, the SRU length (L) is defined as the feret diameter parallel to the longitudinal axis of the absorbent article, and the SRU width (W) is defined as the feret diameter parallel to the lateral axis of the absorbent article. The feret diameter is the distance between two parallel lines, both of which are tangential to the boundary of the SRU, and is recorded to the nearest 0.1 mm.

The interior area of the SRU is recorded to the nearest 0.1 mm$^2$.

Figure 26:
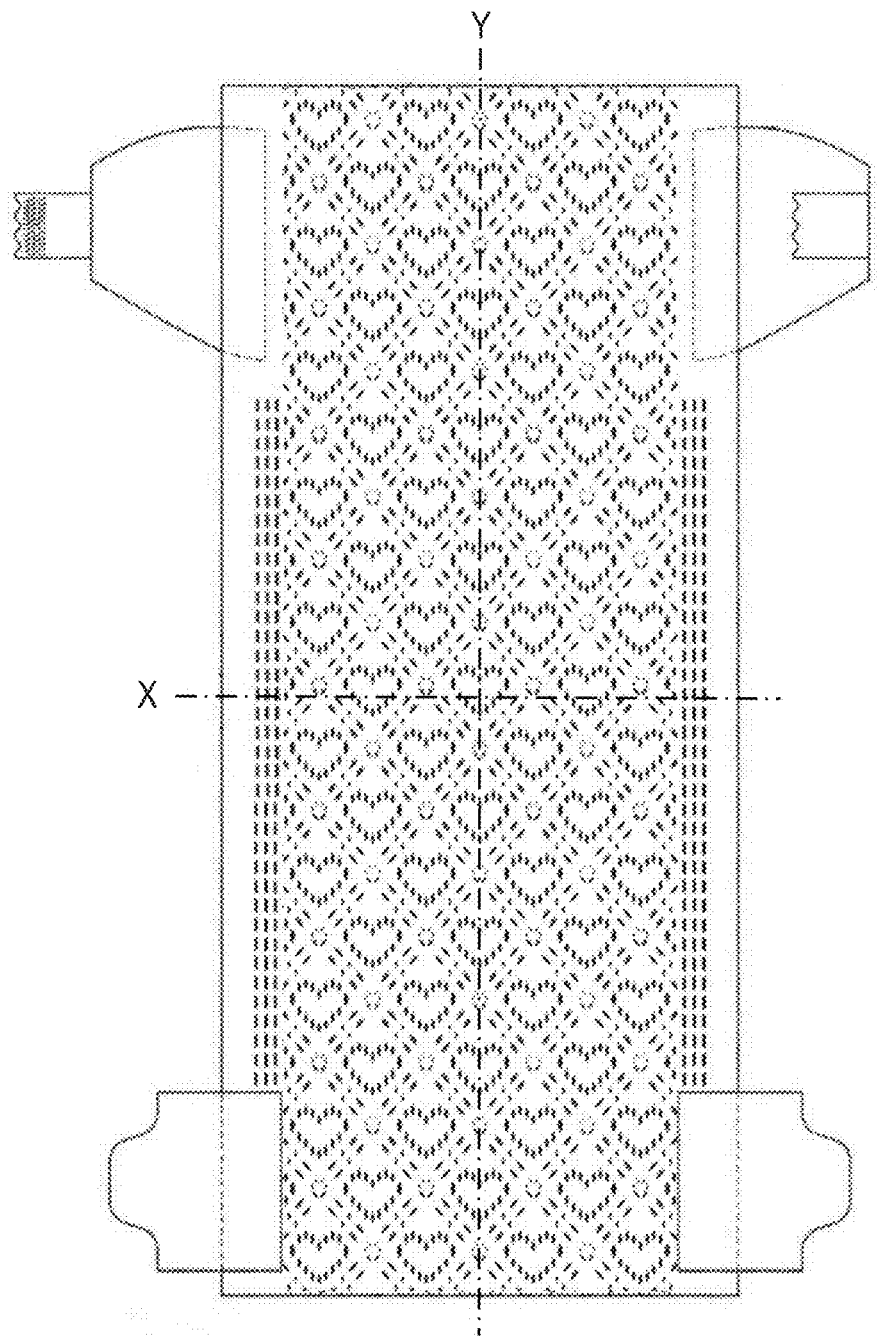
FIG. 26 is an example absorbent article having a topsheet comprising a repeating pattern of apertures comprising a plurality of repeat units linked to the Repeat Unit Measurement Test herein.

Referring to FIG. 26, the total lateral width of the absorbent article is measured along the central lateral axis (line X), and is recorded to the nearest 0.1 mm. The total longitudinal length of the absorbent article is measured along the central longitudinal axis (line Y), and is recorded to the nearest 0.1 mm. The total area of the absorbent article is calculated by multiplying the total absorbent article width by the total absorbent article length, and is recorded to the nearest 0.1 mm$^2$.

The number of SRU's per length of the absorbent article is calculated by dividing the total absorbent article longitudinal length by the SRU length and is recorded to the nearest 0.1 SRU's. The number of SRU's per width of the absorbent article is calculated by dividing the total absorbent article lateral width by the SRU width and is recorded to the nearest 0.1 SRU's. The number of SRU's per total area of the absorbent article is calculated by dividing the total absorbent article area (total absorbent article longitudinal length x total absorbent article lateral width) by the SRU area and is recorded to the nearest 0.1 SRU's.

Repeat this procedure on five separate substantially similar absorbent articles having topsheets with a repeating pattern of apertures comprising a plurality repeat units that are the same or substantially the same, and report each of the measurements as the average of the five replicates.

Aperture Test

Aperture dimensions, Effective Aperture Area, % Effective Open Area, among other measurements, are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif. or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, Va.) prior to acquiring the specimen image. The resulting image is then thresheld, separating open aperture regions from specimen material regions, and analyzed using the image analysis program. All testing is performed in a conditioned room maintained at about 23±2° C. and about 50±2% relative humidity.

Sample Preparation

To obtain a specimen, tape an absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to a machine direction (MD) and a cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) may be used to remove the specimen from the underlying layers if necessary. Five replicates obtained from five substantially similar articles are prepared for analysis. If the apertured layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured or patterned apertured substrate raw material is prepared for testing by extending or activating it under the same process conditions, and to the same extent, as it would be for use on the absorbent article, and then in its extended state adhering it to the steel frame as described above for testing. Condition the samples at about 23° C. ±2° C. and about 50%±2% relative humidity for 2 hours prior to testing.

Image Acquisition

Place the ruler on the scanner bed, oriented parallel to sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of an interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

% Effective Open Area Calculation

Open the calibration image file in the image analysis program and perform a linear distance calibration using the imaged ruler. This distance calibration scale will be applied to all subsequent specimen images prior to analysis. The 8-bit grayscale image is then converted to a binary image in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm², including partial apertures along the edges of the image. Discard any apertures with an area less than 0.3 mm² as "non-effective". Sum the remaining "effective" aperture areas (including whole and partial apertures), divide by the total area included in the image and multiply by 100. Record this value as the % effective open area to the nearest 0.01%.

In like fashion, analyze the remaining four specimen images. Calculate and report the average % effective open area values to the nearest 0.01% for the five replicates.

Effective Aperture Dimension Measurements

Open the calibration image (containing the ruler) file in the image analysis program. Resize the resolution of the original image from 6400 dpi to 640 dpi (approximately 25.2 pixels per mm) using a bicubic interpolation. Perform a linear distance calibration using the imaged ruler. This distance calibration scale will be applied to all subsequent specimen images prior to analysis. Open a specimen image in the image analysis program. Resize the resolution of the original image from 6400 dpi to 640 dpi (approximately 25.2 pixels per mm) using a bicubic interpolation. A distance scale is set according to the linear distance calibration established using the calibration image. The 8-bit grayscale image is then converted to a binary image in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined. Threshold the image at the minimum gray level value to generate a binary image. In the binary image, the apertures appear as black, with a GL value of 255, and specimen as white, with a GL value of 0. Next, two morphological operations are then performed on the binary image. First, a closing (a dilation operation, which converts any white background pixel that is touching, 8-connected, a black aperture region pixel into a black aperture region pixel thereby adding a layer of pixels around the periphery of the aperture region, followed by an erosion operation, which removes any black aperture region pixel that is touching, 8-connected, a white background pixel thereby removing a layer of pixels around the periphery of the aperture region, iterations=1, pixel count=1), which removes stray fibers within an aperture hole. Second, an opening (an erosion operation followed by a dilation operation, iterations=1, pixel count=1), which removes isolated black pixels. Pad the edges of the image during the erosion step to ensure that black boundary pixels are maintained during the operation. Lastly, fill any remaining voids enclosed within the black aperture regions.

Using the image analysis program, analyze each of the discrete aperture regions. During the analysis exclude measurements of partial apertures along the edges of the image, so that only whole apertures are measured. Measure and record all of the individual effective aperture areas, perimeters, feret diameters (length of the apertures) along with its corresponding angle of orientation in degrees from 0 to 180, and minimum feret diameters (width of the apertures). Record the measurements for each of the individual elements areas to the nearest 0.01 mm², the perimeters and feret diameters (length and width), to the nearest 0.01 mm, and angles to the nearest 0.01 degree. Discard any apertures with an area less than 0.3 mm² as "non-effective". Record the number of remaining apertures, divide by the area of the image, and record as the Aperture Density value. The angle of orientation for an aperture aligned with the MD (vertical in the image) will have an angle of 90 degrees. Apertures with a positive slope, increasing from left to right, will have an angle between zero and 90 degrees. Apertures with a negative slope, decreasing from left to right, will have an angle between 90 and 180 degrees. Using the individual aperture angles calculate an Absolute Feret Angle by subtracting 90 degrees from the original angle of orientation and taking its absolute value. In addition to these measurements, calculate an Aspect Ratio value for each individual aperture by dividing the aperture length by its width. Repeat this analysis for each of the remaining four replicate images. Calculate and report the statistical mean and standard deviation for each of the effective aperture dimension, the Absolute Feret Angle, and the Aspect Ratio measurements using all of the aperture values recorded from the replicates. Record the average of the individual Absolute Feret Angle measurements as the Average Absolute Feret Angle value. Calculate and report the % relative standard deviation (RSD)

for each of the aperture dimension, the Absolute Feret Angle, and the Aspect Ratio measurements by dividing the standard deviation by the mean and multiplying by 100.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
a central lateral axis;
a central longitudinal axis extending perpendicular to the central lateral axis;
a topsheet that is liquid permeable, apertured, and nonwoven;
a backsheet that is liquid impermeable; and
an absorbent core disposed at least partially intermediate the topsheet and the backsheet;
the absorbent article having a length along the central longitudinal axis;
the absorbent article having a width along the central lateral axis;
wherein the topsheet comprises a grid of apertures formed by a first plurality of rows of apertures extending in a first direction and a second plurality of rows extending in a second direction, wherein the rows of apertures of the first and second plurality of rows are uniformly spaced, the grid of apertures comprising repeat units, with each repeat unit being defined between (i) centerlines of two adjacent rows of the first plurality of rows, and (ii) centerlines of two adjacent rows of the second plurality of rows that intersect respective ones of the centerlines of the two adjacent rows of the first plurality of rows, wherein the intersections of the centerlines of rows of the first plurality of rows and the centerlines of rows of the second plurality of rows do not comprise an aperture;
wherein each aperture of the first and second plurality of rows comprises a major axis and a minor axis shorter than the major axis, the major axis of all apertures in the first plurality of rows having a first orientation and the major axis of all apertures in the second plurality of rows having a second orientation that is different from the first orientation;
wherein each of the repeat units is substantially the same, and each of the repeat units comprises a central region comprising first apertures and a defined space between the central region and bordering apertures of the adjacent rows of apertures, and wherein the first apertures in each central region are positioned to form a shape of an equity element; and
wherein the repeat units repeat at least along the width of the absorbent article;
wherein the repeat units have a repeat unit length defined between adjacent intersections of the centerlines of the first and second plurality of rows parallel to the central longitudinal axis of the absorbent article, a repeat unit width defined between adjacent intersections of the centerlines of the first and second plurality of rows parallel to the central lateral axis of the absorbent article, and a repeat unit area in a range of about 730 mm$^2$ to 1,400 mm$^2$.

2. The absorbent article of claim 1, wherein the repeat unit width of at least a majority of the repeat units is in the range of about 30 mm to about 70 mm.

3. The absorbent article of claim 1, wherein the repeat unit length of at least a majority of the repeat units is in the range of about 30 mm to about 70 mm.

4. The absorbent article of claim 1, wherein the repeat unit area is in the range of about 730 mm$^2$ to about 1,300 mm$^2$.

5. The absorbent article of claim 1, wherein the repeat units repeat along the width of the absorbent article between about 3 and about 7 times and repeat along the length of the absorbent article between about 4 to about 18 times.

6. The absorbent article of claim 1, wherein a first zone of the topsheet comprises a first subset of the repeat units, and a second zone of the topsheet comprises a second subset of the repeat units, wherein the first subset differs from the second subset in a least one of aperture size, aperture shape, aperture aspect ratio, or aperture pattern.

7. The absorbent article of claim 1, wherein a quantity of the repeat units of the absorbent article is between about 30 to about 180.

8. The absorbent article of claim 1, wherein the repeat units repeat along the width of the absorbent article between about 3 and about 5 times and repeat along the length of the article between about 5 and about 12 times, and wherein a total number of repeat units is between about 35 to about 180, and
wherein at least a majority of the repeat units have a repeat unit area in a range of about 1,100 mm$^2$ to about 1,400 mm$^2$.

9. The absorbent article of claim 1, wherein the equity element is one of a heart, a leaf, a star, a logo, or a brand identifier.

10. The absorbent article of claim 9, wherein the shape of the equity element is not the same as the shape defined by the bordering apertures.

11. The absorbent article of claim 1, wherein at least some of the apertures comprise melt lips on portions of perimeters of the at least some of the apertures.

12. The absorbent article of claim 1, wherein at least some of the apertures are free of melt lips on perimeters of the at least some of the apertures.

13. The absorbent article of claim 1, wherein at least some of the apertures in one or more of the repeat units are different in aperture size or aperture shape than other apertures in the one or more repeat units.

14. The absorbent article of claim 1, wherein at least some of the apertures in one or more of the repeat units are the same in aperture size and aperture shape as other apertures in the one or more repeat units.

15. The absorbent article of claim 1, wherein the central region is at least partially, or fully surrounded by the outer region.

16. The absorbent article of claim 1, wherein the topsheet is multilayered comprising a first layer on a wearer-facing surface of the absorbent article and a second layer disposed between the first layer and the absorbent core.

17. The absorbent article of claim 16, wherein the first layer is hydrophobic, and wherein the second layer is hydrophilic.

18. The absorbent article of claim 16, wherein at least one of the first layer or the second layer comprises spunbond fibers.

19. The absorbent article of claim 16, wherein the first layer comprises spunbond fibers or carded fibers, and wherein the second layer comprises the spunbond fibers or the carded fibers.

20. The absorbent article of claim 1, wherein the topsheet comprises at least one of a whitening additive or an opacifying additive.

\* \* \* \* \*